US005494671A

United States Patent [19]

Lai et al.

[11] Patent Number: 5,494,671
[45] Date of Patent: Feb. 27, 1996

[54] C-TERMINALLY TRUNCATED DENGUE AND JAPANESE ENCEPHALITIS VIRUS ENVELOPE PROTEINS

[75] Inventors: Ching-Jun Lai, Bethesda; Ruhe Men, Chevy Chase; Lei-Ron Jan; Michael Bray, both of Bethesda, all of Md.

[73] Assignee: The United States of America as represented by the Department of Health and Human Services, Washington, D.C.

[21] Appl. No.: 747,785

[22] Filed: Aug. 20, 1991

Related U.S. Application Data

[63] Continuation-in-part of Ser. No. 572,633, Aug. 27, 1990, abandoned.

[51] Int. Cl.[6] ........................ A61K 39/12; A61K 39/295; C07K 14/18

[52] U.S. Cl. .................................... 424/218.1; 424/185.1; 424/186.1; 424/199.1; 424/202.1; 424/204.1; 514/2; 435/69.3; 536/23.72; 530/350; 530/826

[58] Field of Search .................................... 424/89, 185.1, 424/186.1, 218.1, 199.1, 202.1, 204.1; 435/320.1, 235.1, 252.3, 69.1, 69.3; 530/350, 826; 514/2; 536/23.72

[56] References Cited

U.S. PATENT DOCUMENTS 4,810,492 3/1989 Fujita ........................................ 424/88

OTHER PUBLICATIONS

Schlesinger, J. J. et al. "New Approaches to Flavivirus Vaccine Development" Biotechnology 20: 289–307 (1992).
Pizza, et al. Subunit S1 of Pertussis Toxin: Mapping of the Regions Essential For ADP–Ribosyltransferase Activity, Proceedings of the National Academy of Sciences, vol. 85, Oct. 1988.
Mason, P. W. et al (1991) Virology 180: 294–305.
Pincus, S. et al (1992) Virology 187: 290–297.
Deubel, N. et al (1991) Virology 180: 442–447.
Peoples, P. et al (1990) Virus Res. 16: 59–76.
Men, R. et al (1991) J. Virol. 65: 1400–1407.
Bray, et al, "Construction of Intertypic Chimeric Dengue Viruses by Substitution of Structural Protein Genes" *Proc. Natl. Acad. Sci. USA* 88: 10342–6 (1991).
Dulbecco, et al, eds., "Togaviruses, Bunyviruses, and Adenaviruses" *Virology* 1178–96 (1990).
Gentry, et al, "Identification of Distinct Antigenic Determinants on Dengue–2 Virus Using Monoclonal Antibodies" *Am. J. Trop. Med. Hyg.* 31(3): 548–55 (1982).
Holzmann, et al, "A Single Amino Acid Substitution in Envelope Protein E of Tick–Borne Encephalitis Virus Leads to Attenuation in the Mouse Model" *J. Virol.* 64(10): 5156–9 (1990).
Lai, et al, "Infectious RNA Transcribed from Stably Cloned Full–Length cDNA of Dengue Type 4 Virus" *Proc. Natl. Acad. Sci. USA* 88: 5139–43 (1991).
Langford, et al, "Anchoring a Secreted Plasmodium Antigen on the Surface of Recombinant Vaccinia Virus–Infected Cells Increases Its Immunogenicity" *Mol. Cell. Biol.* 6:3191–9 (1986).

(List continued on next page.)

*Primary Examiner*—Christine M. Nucker
*Assistant Examiner*—M. S. Tuscan
*Attorney, Agent, or Firm*—Knobbe Martens Olson & Bear

[57] ABSTRACT

The present invention relates to C-terminally truncated flavivirus envelope proteins 80–81% in size which are more immunogenic than their counterpart full-length proteins. The present invention further relates to recombinant viruses which encode the truncated protein and to host cells infected therewith. Host cells express the truncated protein on their outer membrane and secrete it into the medium. The present invention further relates to vaccines for use against flavivirus infection. The vaccines include either a recombinant vaccinia virus expressing the truncated envelope protein of the present invention, and the truncated envelope protein produced by a recombinant baculovinis.

14 Claims, 14 Drawing Sheets

```
          373                  392    398
           |                    |      |
DEN4       IDSYIVIGVGNSALTLHWFRKGSSIG
DEN2       G..V.I...EPGQ.K.D..K......
DEN3       GE.N....IDDK..IN.Y........
DEN1       GE...VV.A.EK..K.S..K......
```

OTHER PUBLICATIONS

Sabin, A. B., "Recent Advances in Our Knowledge of Dengue and Sandfly Fever" *Amer. J. Trop. Med. Hyg.* 4:198–207 (1955).

Schlesinger, et al, "Clinical and Serologic Response of Man to Immunization with Attenuated Dengue and Yellow Fever Viruses" *J. Immunol.* 77:354–64 (1956).

Schlesinger, et al, "Replication of Togaviridae and Flaviviridae" *Fundamental Virology* 2nd ed:453–76 (1991).

Wisseman, Jr., et al, "Attenuated Living Type 1 Dengue Vaccines" *Amer. J. Trop. Med. Hyg.* 12: 620–3 (1963).

Chambers, Ann. Rev. Microbiol. 44: 649–688 (1990).

Halstead, Science 239: 476–481 (1988).

Mackow et al., Virology 159: 217–228 (1987).

Monath, "Pathobiology of the Flaviviruses" (Schlensinger S., Schlesigner, M. J. (eds). *The Togaviridae and the Flaviviridae* pp. 375–440.

Monath, T. P. "Flaviviruses" *Virology* B. Fields et al. (eds) pp. 955–1044. Raven Press (1985).

Rice, et al., *The New Biologist* 1 (3): 285–296 (1989).

Sabin, Am. J. Trop. Med. Hyg. 1:30–50 (1952).

Westaway, Adv. Virus. Res. 33: 45–90 (1987).

Zhao, et al., Virology 155:77–88 (1986).

Bancroft, W. et al., Pan Am. Hlth. Org. Sci. Publ. 375:173–178 (1979).

Bhamarapravati, N. et al., Bull. WHO. 65:189–195 (1987).

Bray, M. et al., J. Virol. 63:2853–2856 (1989).

Castle, E. et al., Virology 145:227–236 (1985).

Chakrabartri, S., Mol. Cell. Biol. 5:3403–3409 (1985).

Cheng, H. L., et al., Nature 296:410–415 (1982).

Clarke, D. H., J. Exp. Med. 111:21–23 (1960).

Coia, G. et al., J. Gen Virol., 69:1–21 (1988).

Deubel, V. et al., Virology 155:365–377 (1986).

Falgout, B. et al., J. Virol. 63: 1852–1860 (1989).

Gruenberg, A. et al., J. Gen Virol. 69: 1391–1398 (1988).

Hahn, Y. S. et al., Virology 162: 167–180 (1988).

Heinz, F. X., Adv. in Virus Res. 31: 103–168 (1986).

Henchal, E. A. et al., Am. J. Trop. Med. Hyg.

Hoke, et al., Am. J. Trop. Med. Hyg. 43:219–226 1990).

Hori, H. et al., J. Virology 64:4573–4577 (1990).

Irie, A. et al., Gene 75: 197–211 (1989).

Kehry, M. et al., Cell 21: 393–406 (1980).

Kilpatrick, D. R. et al., J. Biol. Chem. 262:16116–16121 (1987).

Mandl, C. W., J. Virol. 63: 564–571 (1989).

Marchette, N. J., Am. J. Trop. Med. Hyg. 43(2): 212–218 (1990).

Markoff, L., J. Virol. 63: 3342–3352 (1989).

Markoff, L. J. et al. "Antigenic analysis of the dengue virus envelope glycoprotein using synthetic peptides", pp. 161–165. In H. Ginsberg et al. (ed.) *Vaccines 88: New chemical and genetic approaches to Vaccination.* Cold Spring Harbor Laboratory, Cold Spring Harbor, NY (1988).

Mason, P. W. et al., Virology 161: 262–267 (1988).

McKee, K. T., et al., Am. J. Trop. Med. Hyg. 36: 435–442 (1987).

Nowak, T. et al., Virology 156: 127–137 (1987).

Osatomi, K. et al., Virology 176: 643–647 (1990).

Osatomi, K. et al., Virus Genes 2:99–108 (1988).

Paterson, et al., Cell 48:441–452 (1987).

Pletnev, et al., Virology 174:250–263 (1990).

Puddington, L., et al., J. Cell Biol. 102:2147–2157 (1986).

Rice, C. M., Science 229: 726–733 (1985).

Roehrig, J. T. et al., Virology 128: 118–126 (1983).

Roehrig, J. T. et al., "Synthetic peptide vaccine strategy for inducing flavivirus immunity" In: *Vaccines 89: Modern Approaches to New Vaccines Including Prevention of AIDS.* Lerner, R. A. et al. (eds.) pp. 347–350. Cold Spring Harbor Laboratory (1989).

Stollar, V., Virology 39: 426–438 (1969).

Sumiyoshi, H., Virology 161: 497–510 (1987).

Sweet et al., J. Immunol. 73: 363–373 (1954).

Wengler, et al., Virology 147: 264–274 (1985).

Winkler, G. et al., i J. Gen. Virol., 68:2239–2244 (1987).

Zhang, Y. M. et al, J. Virol. 62: 3027–3031 (1988).

Zhao et al., J. Virol. 61: 4019–4022 (1987).

Harrison, et al. Infect. Immun. 18:151–156 (1977).

FIG. 5A
FIG. 5B
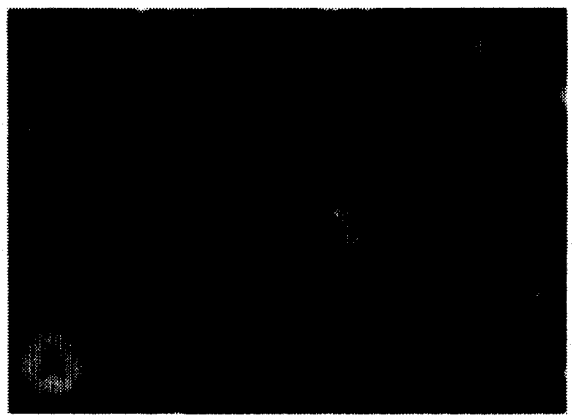
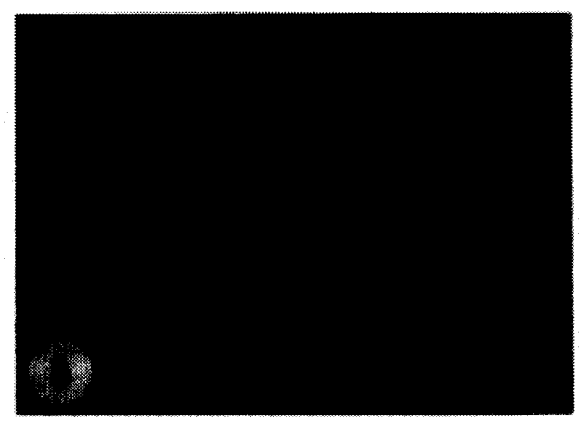
FIG. 5C
FIG. 5D

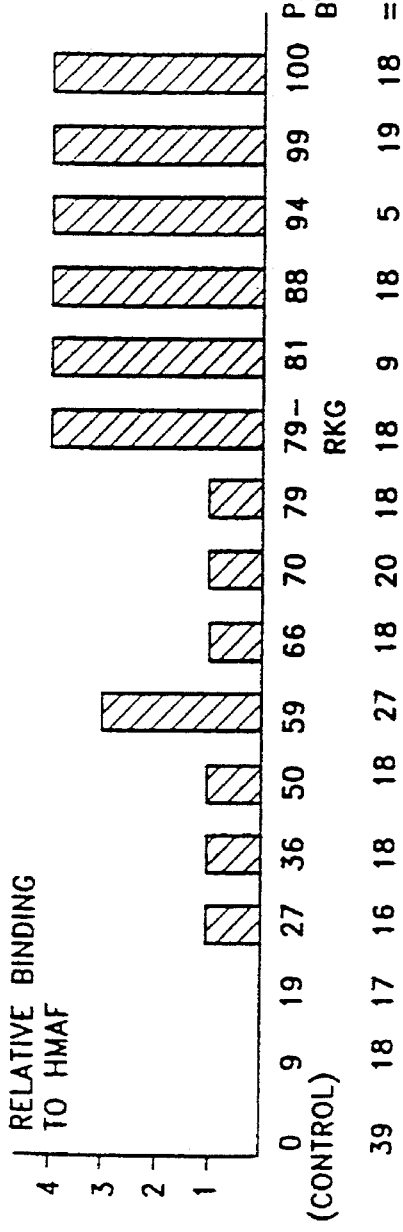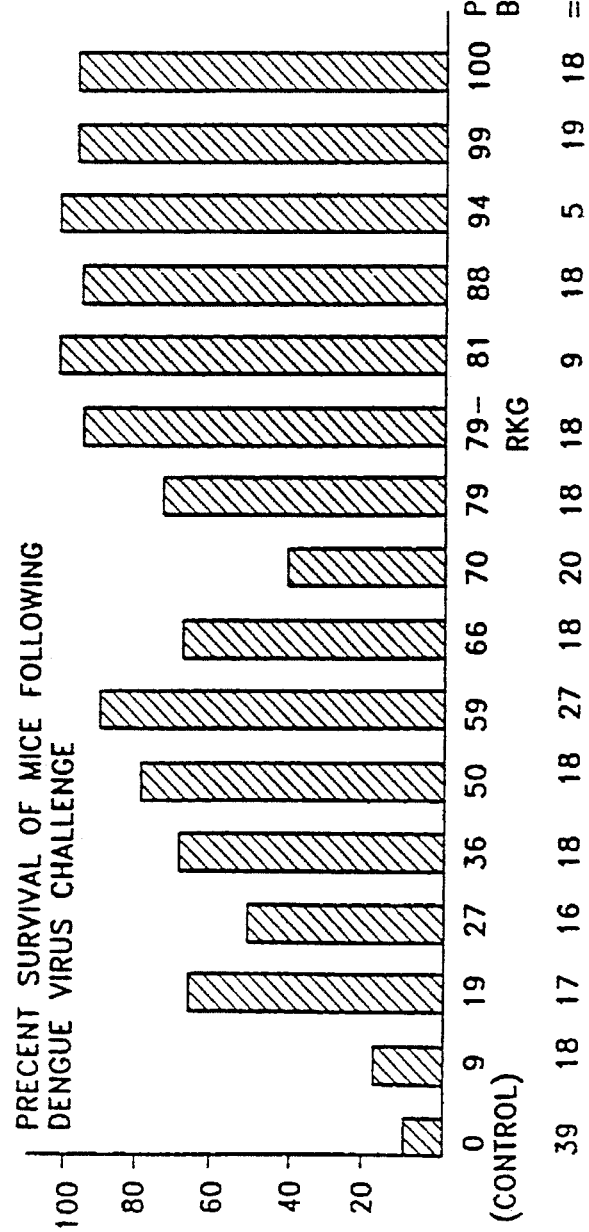
FIG. 7A
FIG. 7B

```
             373                    392   398
              |                      |     |

DEN4         IDSYIVIGVGNSALTLHWFRKGSSIG

DEN2         G..V.I...EPGQ.K.D..K......

DEN3         GE.N....IDDK..IN.Y........

DEN1         GE...VV.A.EK..K.S..K......
```

DEN4    IDSYIVIGVGNSALTLHWFRKGSSIG

JE      G.....V.R.DKQ.NH..HKA..TL.

|                      |      |
          379                    398    404
```

FIG. 11

FIG. 13A
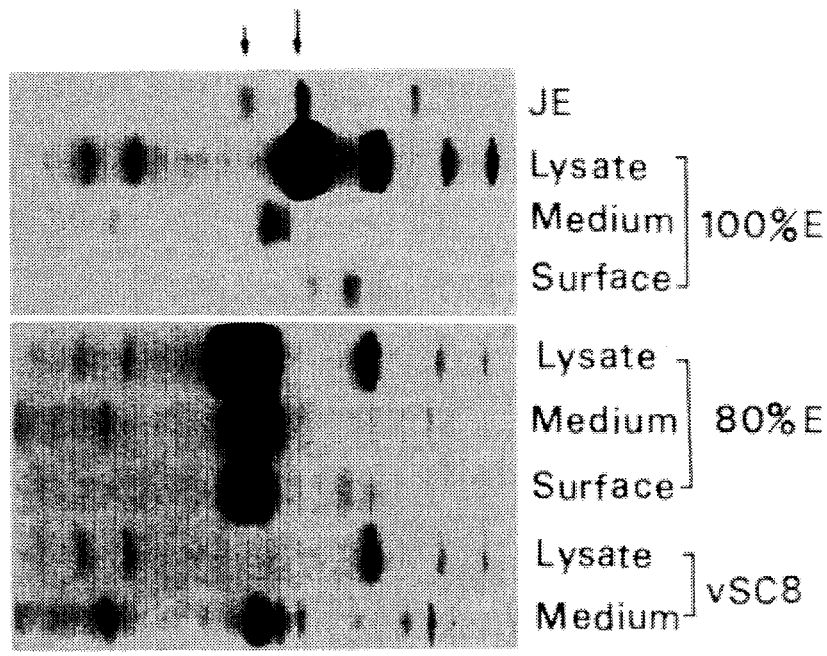
FIG. 13B
FIG. 13C
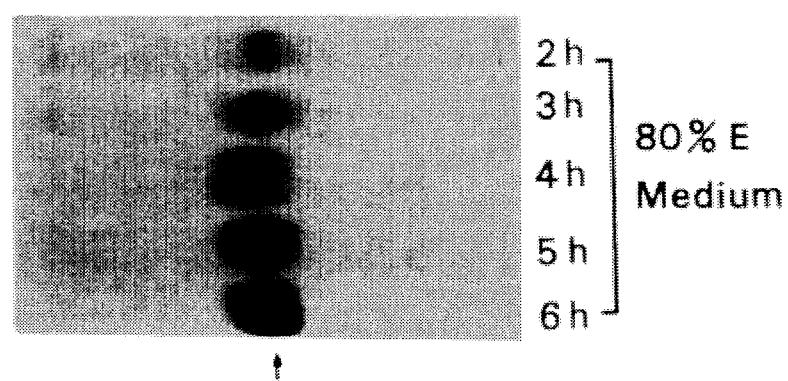

C-TERMINALLY TRUNCATED DENGUE AND JAPANESE ENCEPHALITIS VIRUS ENVELOPE PROTEINS

This is a continuation-in-part application of application Ser. No. 07/572,633 filed Aug. 27, 1990, abandoned, which is hereby incorporated in its entirety.

BACKGROUND OF THE INVENTION

1. Field of the Invention

The present invention relates to flavivirus E proteins and their use in vaccines against flavivirus infection.

2. Background Information

Endemic dengue caused by one or more of the four types of dengue viruses is a major public health problem in many tropical and subtropical areas. In addition, sporadic dengue epidemics at times involving over a million individuals, continue to occur in these regions. Many other members of the flavivirus family are also etiologic agents of severe diseases such as yellow fever, Japanese encephalitis, St. Louis encephalitis, and tick-borne encephalitis.

Epidemic outbreaks, for example, caused by Japanese encephalitis virus (JEV) continue to pose serious public health problems in the densely populated regions of tropical and subtropical Asia. Transmitted by species of the Culex genus mosquitos, the disease is clinically manifested as encephalitis, often severe and with a high mortality rate among young children and elderly people. Further, permanent neurological sequelae of different severity can occur in a high percentage of patients who survive. JEV also infects domestic animals such as swine and horses. During the last two decades, immunization using an inactivated JEV vaccine has brought the disease under control in Japan, Korea and Taiwan. However, because of the high cost of manufacturing the vaccine, it is not readily available to those countries where it is needed the most.

Flaviviruses, including the dengue virus and the JEV, contain only three structural proteins, that is, a capsid protein (C, mol. wt. 12–14 kd) which binds to the positive strand genomic RNA forming the nucleocapsid, and two membrane associated proteins termed the small membrane protein (M, mol. wt. 7–8 kd) and the large membrane protein also called envelope glycoprotein (E, mol. wt. 55–60 kd) (Stollar, V. 1969. Studies on the nature of dengue viruses. IV The structural proteins of type 2 dengue virus. Virology 39:426–438). The envelope glycoprotein is the major virion antigen responsible for virus neutralization by specific antibodies and for several important antigenic properties such as binding to flavivirus-, dengue complex-, and type-specific antibodies (Clarke, D. H. 1960. Antigenic analysis of certain group B arthropod-borne viruses by antibody absorption. J. Exp., Med. 111:21–32. Roehrig, J. T., J. H. Mathew, and D. W. Trent. 1983 Identification of epitopes on the E glycoprotein of St. Louis encephalitis virus using monoclonal antibodies. Virology 128:118–126). Dengue and other flavivirus E's also exhibit a hemagglutinating activity that is presumably associated with virus attachment to the cell surface and subsequent virus uncoating (Sweet, B. H., and A. B. Sabin. 1954. Properties and antigenic relationships of hemagglutinins associated with dengue viruses. J. Immunol. 73;363–373). The full-length dengue type 4 virus E sequence contains 494 amino acids including two hydrophobic regions at the C-terminus, 15 amino acids and 24 amino acids in length, separated by an arginine. These hydrophobic sequences may serve to interact with the lipid membrane during virus assembly. Evidence from limited protease digestion of tick-borne encephalitis virus E glycoprotein suggest that the hydrophobic C-terminus is inserted into the lipid membrane exposing the bulk of the N-terminus of E on the virion surface.

The full-length E of dengue type 4 virus contains 12 cysteine residues, all of which are conserved in at least 20 flavivirus E's that have been sequenced. The most C-terminal cysteine in dengue type 4 E is at position 333 of the E sequence. Thus, 67% or more of the N-terminal E should contain all 12 cysteine residues. In flavivirus West Nile E, each of the 12 cysteines appeared to be involved in di-sulfide bond formation (Nowak, T., and G. Wengler 1987. Analysis of disulfides present in the membrane proteins of the West Nile flavivirus. Virology 156:127–137). In dengue type 4 E, two potential N-linked glycosylation sites are located at positions 67 and 153 and a third N-glycosylation site is present at position 471 within the C-terminal hydrophobic region that is probably not used. 31% N-terminal E contains both potential glycosylation sites. However, the E glycoproteins of 2 flaviviruses, West Nile virus and Kunjin virus, lack glycosylation sites suggesting that N-glycosylation is not essential to the antigenic, structural, and functional integrity of the flavivirus envelope glycoprotein (Coia, G., M. D. Parker, G. Speight, M. E. Byrne, and E. G. Westaway. 1988. Nucleotide and complete amino acid sequences of Kunjin virus: definitive gene order and characteristics of the virus-specified proteins. J. Gen. Virol. 69:1–21; and Wengler, G., E. Castle, U. Leidner, T. Nowak, and G. Wengler. 1985. Sequence analysis of the membrane protein v3 of the flavivirus West Nile virus and of its gene. Virology 147:264–274).

Results of epitope mapping with a library of monoclonal antibodies indicate that the antigenic structure of dengue E is similar to that of other flavivirus E's that contain several distinct antigenic sites as defined by serological specificity, functional activity, and competitive binding assay (Henchal, E. A., J. M. McCown, D. S. Burke, M. C. Sequin, and W. E. Brandt. 1985. Epitopic analysis of antigenic determinants on the surface of dengue-2 virus using monoclonal antibodies. Am. J. Trop. Med. Hyg. 34:162–169; and Heinz, F. X. 1986. Epitope mapping of flavivirus glycoproteins. Advance in Virus Research Vol. 31, pp. 103–168, K. Muramorosch, F. A. Murphy, and A. J. Shatkin (ed.)). All E's appears to be similar consisting of at least three nonoverlapping antibody-binding domains (antigenic sites). A majority of these sites are dependent on the protein conformation since fragmentation of E by protease digestion or chemical disruption of disulfide bonds abolishes antibody binding (Mandl, C. W., F. Guirakhoo, H. Holzmann, F. X. Heinz, and C. Kunz. 1989. Antigenic structure of the flavivirus envelope protein E at the molecular level, using tick-borne encephalitis virus as a model. J. Virol. 63:564–571; and Winkler, G., F. X. Heinz, and C. Kunz. 1987. Characterization of a disulfide bridge-stabilized antigenic domain of tick-borne encephalitis virus structural glycoprotein. J. Gen. Virol. 68:2239–2244). Moreover, the identification of two or more sites involved in neutralization, hemagglutination inhibition or passive protection indicates that these functions are not localized to a single domain on the E glycoprotein.

More recently, complete or nearly complete sequences of the genome of several dengue viruses as well as other major flaviviruses have been determined and their polyprotein sequences deduced (Castle, E., T. Nowak, U. Leidner, G. Wengler, And G. Wengler. 1985. Sequence analysis of the viral core protein and the membrane-associated proteins V1 and NV2 of the flavivirus West Nile virus and of the genome sequence for these proteins. Virology 145:227–236; Coia, G., M. D. Parker, G. Speight, M. E. Byrne, M. and E. G. Westaway. 1988. Nucleotide and complete amino acid sequences of Kunjin virus: definitive gene order and characteristics of the virus-specified proteins. J. Gen. Virol. 69:1–21; Deubel, V., R. Kinney, and D. W. Trent. 1986. Nucleotide sequence and deduced amino acid sequence of the structural proteins of dengue type 2 virus, Jamaica genotype. Virology 155:365–377; Gruenerg, A., W. S. Woo, A. Biedrzyca, and P. J. Wright. 1988. Partial nucleotide sequence and deduced amino acid sequence of the structural proteins of dengue virus type 2, New Guinea C and PUO-218 strains. J. Gen. Virol. 69:1391–1398; Hahn, Y. S., R. Galler, T. Hunkapiller, J. M. Dalyryple, J. H. Strauss, and E. G. Strauss. 1988. Nucleotide sequence of dengue 2 RNA and comparison of the encoded proteins with those of other flaviviruses. Virology. 162:167–180; Irie, K., P. M. Mohan, Y. Sasaguri, R. Putnak, and R. Padmanabhan. 1989. Sequence analysis of cloned dengue type 2 genome (New Guinea-C strain). Gene 75:197–211; Mackow, E., Y. Makino, B. Zhao, Y. -M. Zhang, L. Markoff, A. Buckler-White, M. Guiler, R. M. Chanock, and C. -J. Lai. 1987. The nucleotide sequence of dengue type 4 virus: analysis of genes coding for nonstructural proteins. Virology 159:217–228; Mason, P. W., P. C. McAda, T. L. Mason, and M. J. Founier. 1987. Sequence of the dengue-1 virus genome in the region encoding the three structural proteins and the major nonstructural protein NS1. Virology 161:262–267; Osatomi, K., I. Fuke, D. Tsuru, T. Shiba, Y. Sakaki, H. Sumiyoshi. 1988. Nucleotide sequence of dengue type 3 virus genomic RNA encoding viral structural proteins. Virus Genes 2:99–108; Pletnev, A. G., V. Yamshchikov, and V. M. Blinov. 1990. Nucleotide sequence of the genome and complete amino acid sequence of the polyprotein of tick-borne encephalitis virus. Virology 174:250–263; Rice, C. M., E. M. Lenches, S. R. Eddy, S. J. Shin, R. L. Sheets, and J. H. Strauss. 1985. Nucleotide sequence of yellow fever virus: implications for flavivirus gene expression and evaluation. Science 229:726–733; Sumiyoshi, H., C. Mori, I. Fuke, K. Morita, S. Kuhara, J. Kondou, Y. Kikuchi, H. Nagamutu, and A. Igarashi. 1987. Complete nucleotide sequence of the Japanese encephalitis virus genome RNA. Virology 161:497–510; Wengler, G., E. Castle, U. Leidner, T. Nowak, and G. Wengler. 1985. Sequence analysis of the membrane protein v3 of the flavivirus West Nile virus and of its gene. Virology 147:264–274; and Zhao, B., E. Mackow, A. Buckler-White, L. Markoff, R. M. Chanock, C. -J. Lai, and Y. Makino. 1986. Cloning full-length dengue type 4 virus DNA Sequences: analysis of genes coding for structural proteins. Virology 155;77– 88). Comparison of amino acid sequences showed that there is significant sequence homology among the E glycoproteins of different flaviviruses. For example, between dengue type 4 virus and JEV, the amino acid homology is 44% whereas the amino acid homology varies from 60–74% among degne viruses. As expected, sequence homology of E was observed to be greatest among the different dengue serotypes.

Despite four decades of research effort, a safe and effective vaccine against flaviviruses such as dengue is still not available. However, several new strategies for vaccine development based upon the use of cloned dengue cDNA for synthesis of dengue protective antigens have yielded encouraging results. During recent studies, expression of cloned DNA that codes for the dengue type 4 virus structural proteins (C, M, and E) together with nonstructural protein NS1 was achieved during infection of: (i) eucaryotic cells with a vaccinia virus-dengue recombinant or (ii) insect cells with a baculovirus-dengue recombinant (Zhao, B., G. Prince, R. Horswood, K. Eckels, P. Summer, R. M. Chanock, and C. -J. Lai. 1987. Expression of dengue virus structural proteins and nonstructural protein SN1 by a recombinant vaccinia virus. J. Virol 61:4019– 4022; and Zhang, Y. M., E. P. Hayes, T. C. McCarty, D. R. Dubois, P. L. Summers, K. H. Eckels, R. M. Chanock, and C. -J. Lai. 1988. Immunization of mice with dengue structural proteins and nonstructural protein NS1 expressed by baculovirus recombinant induces resistance to dengue encephalitis. J. Virol. 62:3027–3031). The vaccinia virus recombinant system was also employed to separately express dengue E or NS1 glycoprotein (Bray, M., B. Zhao, L. Markoff, K. H. Eckels, R. M. Chanock, and C. -J., Lai. 1989. Mice immunized with recombinant vaccinia virus expressing dengue 4 virus structural proteins with or without nonstructural protein NS1 are protected against fatal dengue virus encephalitis. J. Virol. 63:2853–2856; and Falgout, B., R. M. Chanock, and C. -J. Lai. 1989. Proper processing of dengue virus nonstructural glycoprotein NS1 requires the N-terminal hydrophobic signal sequence and the downstream nonstructural protein NS2A. J. Virol. 63:1852–1860). Infection of mice with a vaccinia virus recombinant expressing full-length E and NS1 glycoproteins [v(C-M-E-NS1-NS2A)], 93% of the N-terminal E sequence [v(93% E)], or only NS1 [v(NS1-NS 2A)] induced complete or almost complete resistance to fatal encephalitis resulting from intracerebral inoculation of dengue type 4 virus (Bray, M., B. Zhao, L. Markoff, K. H. Eckels, R. M. Chanock, and C. -J., Lai. 1989. Mice immunized with recombinant vaccinia virus expressing dengue 4 virus structural proteins with or without nonstructural protein NS1 are protected against fatal dengue virus encephalitis. J. Virol. 63:2853–2856; and Falgout, B., M. Bray, J. J. Schlesinger, and C. -J. Lai 1990. Immunization of mice with recombinant vaccinia virus expressing authentic dengue virus nonstructural protein NS1 protects against lethal dengue encephalitis. J. Virol. 64: 4356–4363, 1990). Immunization of mice with baculovirus recombinant expressed E and NS1 also induced a similar level of resistance (Zhang, Y. M., E. P. Hayes, T. C. McCarty, D. R. Dubois, P. L. Summers, K. H. Eckels, R. M. Chanock, and C. -J. Lai. 1988. Immunization of mice with dengue structural proteins and nonstructural protein NS1 expressed by baculovirus recombinant induces resistance to dengue encephalitis. J. Virol. 62:3027–3031). However, v(C-M-E-NS1-NS2A) or v(93% E) or the baculovirus recombinant-infected cell lysate containing expressed E, consistently failed to induce detectable antibodies to E or induced only a very low level of such antibodies in mice (Bray, M., B. Zhao, L. Markoff, K. H. Eckels, R. M. Chanock, and C. -J., Lai. 1989. Mice immunized with recombinant vaccinia virus expressing dengue 4 virus structural proteins with or without nonstructural protein NS1 are protected against fatal dengue virus encephalitis. J. Virol. 63:2853–2856; and Zhang, Y. M., E. P. Hayes, T. C. McCarty, D. R. Dubois, P. L. Summers, K. H. Eckels, R. M. Chanock, and C. -J. Lai. 1988. Immunization of mice with dengue structural proteins and nonstructural protein NS1 expressed by baculovirus recombinant induces resistance to dengue encephalitis. J. Virol. 62:3027–3031). A more recent study showed that monkeys immunized with baculovirus-expressed E also failed to develop antibodies to E as detected by radioimmunoprecipitation and presumably for this reason only partial resistance to intravenous dengue virus challenge was induced (Lai, C. -J., Y. -M. Zhang, R. Men, M. Bray, R. M. Chanock, D. R. Dubois, and K. H. Eckels. 1990. Immunization of monkeys with baculovirus recombinant-expressed dengue envelope and NS1 glycoproteins induces partial resistance to challenge with homotypic dengue virus, p. 119–124. In F. Brown, R. M. Chanock, H. S. Ginsberg, and R. Lerner (ed.), Vaccines 90: Modern approaches to new vaccines including prevention of AIDS. Cold Spring Harbor Laboratory, Cold Spring Harbor, N.Y.).

There has also been a recent report of a live, attenuated dengue-2 candidate vaccine, which induced neutralizing antibodies in 10 human volunteers, who suffered no untoward effects of immunization (Immunization with a live attenuated dengue-2 virus candidate vaccine, 16681-PDK53: clinical, immunological and biological responses in adult volunteers. *Bull. Who* 65:189–195, 1987). However, this report suggests that the candidate vaccine is heat-labile, as the vaccine was stored at −80° C. prior to use, and aliquots for virus titration were kept on ice following immunization.

Such a vaccine would probably require a continuous "cold chain" for use in tropical areas. There is no basis for estimating the cost per dose for a live, attenuated vaccine, but it may be several dollars, a possibly prohibitive amount for mass immunization in "third world" nations. A vaccinia recombinant vaccine producing dengue virus antigens should share the characteristics of the vaccinia virus vaccine proven during successful global smallpox eradication campaign. That is, the vaccine should be safe, heat stable and easily administered, and have a low cost per dose. Thus, the low immunogenicity of E constitutes a major obstacle to the development of an effective dengue vaccine produced by recombinant DNA technology.

SUMMARY OF THE INVENTION

It is an object of the present invention to provide safe and effective vaccines against flaviviruses for humans and animals.

Various other objects and advantages of the present invention will become apparent from the drawings and the following description of the invention.

In one embodiment, the present invention relates to a vaccine for humans and animals against flavivirus infection comprising a recombinant virus expressing a C-terminally truncated flavivirus envelope protein in an amount sufficient to induce immunity against the infection and a pharmaceutically acceptable carrier, wherein the truncated protein is intracellularly accumulated, or extracellularly secreted, or expressed on the outer membrane of infected cells.

In another embodiment, the present invention relates to a vaccine for humans and animals against flavivirus infection comprising a recombinantly expressed truncated flavivirus envelope protein in an amount sufficient to induce immunity against the infection and a pharmaceutically acceptable carrier.

In a further embodiment, the present invention relates to a DNA construct comprising a DNA segment encoding a C-terminally truncated flavivirus protein and a vector, wherein the truncated protein is expressed intracellularly, extracellularly, or on the outer membrane of host cells expressing the construct.

In another embodiment, the present invention relates to a recombinant virus encoding a C-terminally truncated flavivirus envelope protein which is expressed intracellularly, extracellularly, or on the outer membrane of host cells infected with the virus. The present invention also related to host cells productively infected with the recombinant virus of the present invention.

BRIEF DESCRIPTION OF THE DRAWINGS

FIG. 5 shows detection of truncated E's of dengue virus on the surface of recombinant vaccinia virus infected cells. An immunofluorescence assay on live cells was performed. (A) Shows cells infected with v(79% E-RKG); (B) shows cells infected with v(81% E); (C) shows cells infected with v(59% E); and (D) shows cells infected with v(100% E).

FIG. 7 displays the relationship of protective efficacy of vaccinia virus dengue E recombinants to overall antigenicity of expressed E products. The top panel shows relative binding of the expressed E products to dengue virus hyperimmune mouse ascitic fluid (HMAF) as detected by radio-immunoprecipitation. On a scale of 1 to 4, the highest number was assigned to the E products which exhibit high HMAF binding affinity, and the lower numbers (1 and 3) to E's which bind less efficiently to HMAF. The lower panel shows the cumulative protection rates as expressed by percent survival following dengue virus challenge of mice immunized with various vaccinia recombinants expressing 9– 100% dengue E's. The results were derived from 4 separate mouse protection studies. The total number of mice tested for each recombinant is indicated.

FIG. 9 shows the alignment of amino acid sequences in the antigenically critical region dengue type 4 and three other dengue serotype E glycoproteins. The 26 amino acid sequence (positions 373–398) of denge type 4 glycoprotein was compared with the corresponding E sequences of dengue type 1, type 2, and type 3 viruses. Arg (R) at position 392 at the C-terminus of dengue type 4 80% E has been shown to be critical for the antigenic structure displaying a high affinity binding by HMAF (in this invention).

FIG. 11 Alignment of sequences in the antigenically critical region of dengue type 4 and Japanese encephalitis virus envelope glycoproteins. The 26 amino acid sequence (positions 373–398) of dengue type 4 E glycoprotein was compared with the corresponding sequence (positions 379–404) of JE E glycoprotein. Arg at position 392 of dengue type 4 E has been shown to be critical for the antigenic structure (see FIG. 3). A conserved amino acid found between the two viruses is indicated by a dot in the JE sequence.

FIG. 13 JE virus C-terminally truncated E is expressed on the cell surface and extracellularly secreted. (A) Infection of CV-1 cells and radio-labeling were the same as in FIG. 12. JE E produced in the lysate, in the medium fluid, or on the cell surface was analyzed on a polyacrylamide gel. Note that the long exposure of the film was intended to reveal in the surface lane a labeled protein band identified as 100% E based on co-migration with the full-length E indicated by the long arrow. C-terminally truncated E (80% E) indicated by the short arrow is present in the medium and on the surface. Other minor bands on the gel are background since they are also present in the corresponding fractions of the vSC8 control. (B) Following a 2 hr radio-labeling, medium from v (JE, 80% E)-infected cells was collected at various times indicated and analyzed as described herein.

DETAILED DESCRIPTION OF THE INVENTION

Figure 1:
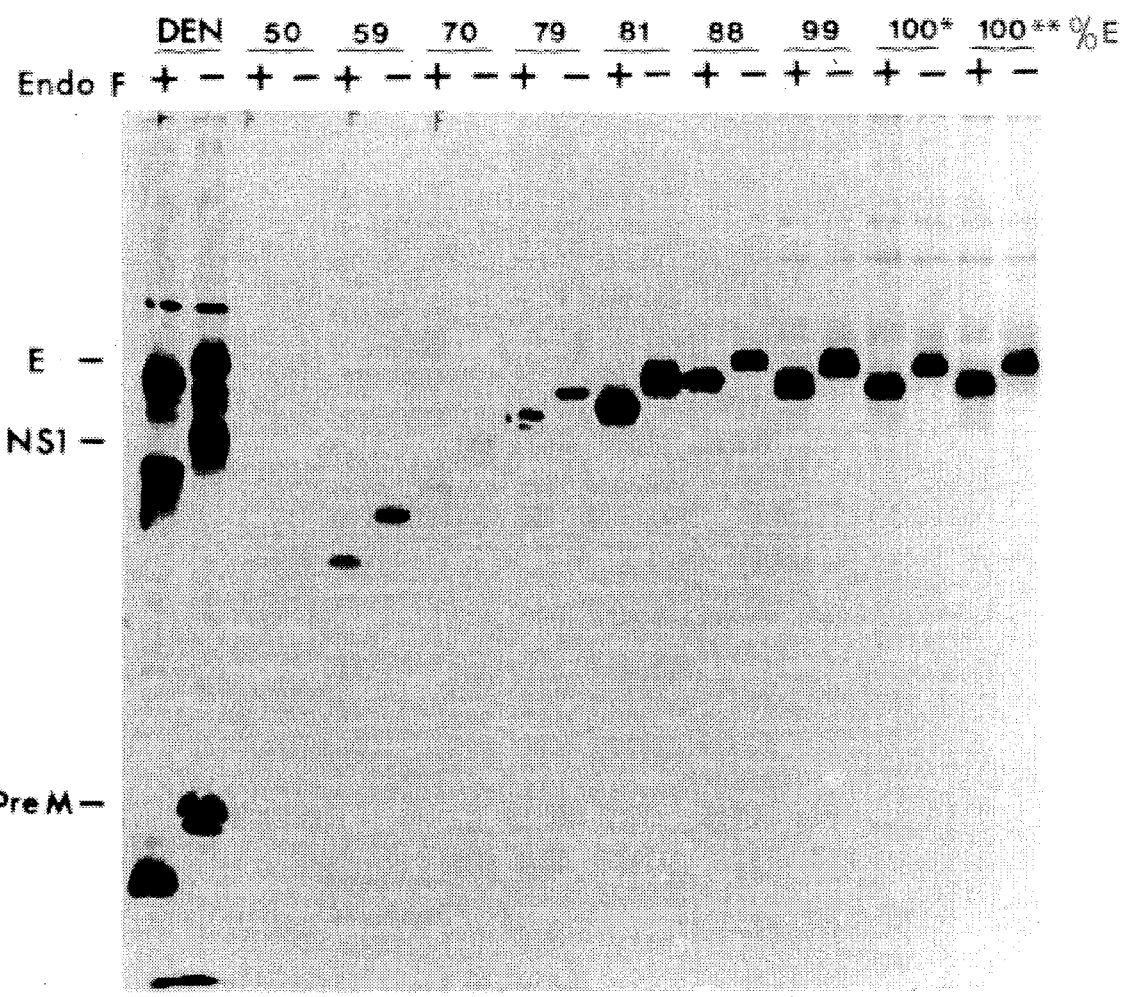
FIG. 1 shows an analysis of dengue C-terminally truncated and the full-length envelope glycoproteins expressed by recombinant vaccinia viruses. $^{35}$S-methionine labeled lysates of CV-1 cells infected with various recombinant virus constructs were prepared and immunoprecipitated with a dengue virus hyperimmune mouse ascitic fluid (HMAF). Each immunoprecipate was divided into two aliquots: one was treated with endoglycosidase F (+); the other remained untreated (−). Samples were subsequently analyzed on SDS-12% polyacrylamide gel. The predicted length of the N-terminal envelope (E) sequence expressed by each recombinant is indicated. Two recombinants, expressing the full length E plus 4 amino acids of NS1, and the full-length E plus 22 amino acids of NS1, were designated 100*% and 100**%, respectively. The HMAF precipitate of $^{35}$S-methionine labeled lysate of dengue virus infected cells was used as dengue protein size markers (DEN).

Dengue E glycoprotein, like other flavivirus E glycoproteins, plays an important role in various stages of viral infection and the development of protective immunity. In the investigations leading to the present invention, the sequence of the dengue type 4 virus envelope protein (E) was analyzed by systematic C-terminal deletion and expression of the resulting truncated E product in a vaccinia virus recombinant in an attempt to delineate E sequences responsible for inducing resistance in mice and to improve the immunogenicity of this major viral protein antigen. Unlike full-length E, several of the C-terminal truncated E products were secreted extracellularly or accumulated on the cell surface and most importantly the later property was associated with increased immunogenicity. Similarly truncated dengue type 2 virus and Japanese encephalitis virus envelope proteins expressed by recombinant vaccinia virus also proved to be more immunogenic than the full length proteins. Using the high yielding baculovirus-insect cell expression system the truncated envelope glycoprotein of dengue type 4 or type 2 virus was also extracellularly secreted by recombinant virus infected cells.

Accordingly, the present invention relates to DNA constructs encoding a truncated flavivirus E protein, for example, dengue type 4, dengue type 2 or Japanese encephalitis virus E. DNA constructs to which the present invention relates comprise a vector and a DNA segment encoding a sufficient amount of the N-terminus sequence of a flavivirus E protein so that expression of the protein alters its intracellular processing pathway resulting in accumulation on the outer membrane of the cell. The truncated protein may also be secreted extracellularly. For example, the DNA segment may encode at least 80% of the N-terminus sequence of dengue type 4 virus an E protein, preferably between 80 and 81%. As used herein 80% E refers to 79% of the N-terminus sequence of dengue type 4 virus E plus R, RK, RKG, RKGS, or RKGSS (amino acids designated by the standard single letter code). Similarly, 80% of other flavivirus E's refer to the E molecules corresponding in size to the dengue type 4 80% E sequence. Suitable vectors for use in the present invention include, but are not limited to, the vaccinia virus vector and baculovirus vector.

The DNA constructs of the present invention are used to generate recombinant viruses such as, for example, recombinant vaccinia viruses and recombinant baculoviruses using methods known in the art. Thus, the present invention further relates to recombinant viruses encoding the truncated E protein of the present invention. For example, a recombinant vaccinia virus encoding a truncated dengue type 4, or type 2, or JEV E protein (preferably, encoding about 80% E) can be produced using the construct of the present invention.

In another embodiment, the present invention relates to eukaryotic host cells producing the truncated E protein. Suitable host cells include, but are not limited to, mammalian cells such as, CV-1 and TK⁻143 cells, and insect cells such as, *Spodoptera frugiperda* cells. In particular when the recombinant virus is a baculovirus, the host cell must be an insect cell. Host cells are infected with the recombinant viruses of the present invention and are cultured under conditions allowing expression of the encoded truncated E protein. Some of the expressed truncated flavivirus E protein is retained on the outer membrane of the cell and some of it is also secreted from the cell.

For example, mammalian cells infected with a recombinant vaccinia virus expressing the truncated dengue type 4 E or JEV E protein were shown to accumulated the truncated protein on their cell surface by indirect immunofluorescence and to secrete the truncated protein extracellularly by radio immunoprecipitation. Further, insect cells infected with a recombinant baculovirus of the present invention also express the truncated protein into the medium fluid.

The present invention also relates to recombinantly produced truncated flavivirus E protein and to antibodies specific therefor. Preferably, the recombinantly produced E protein is between 80 and 81% of the N terminus sequence of the naturally occurring E protein, or an allelic variation thereof. The recombinantly produced protein may be glycosylated or unglycosylated. One skilled in the art, without undue experimentation, can easily modify, partially remove or completely remove the natural glycosyl groups from the E protein of the present invention using standard methodologies.

The flavivirus E proteins of the present invention are truncated at the C-termini so that when expressed in host cells, some of the proteins is extracellularly secreted and some is retained on the outer membrane of the cell. The truncated proteins are more immunogenic and protective than the counterpart full-length proteins or than shorter proteins which are retained intracellularly. In protection studies, mice inoculated with recombinant vaccinia virus encoding truncated dengue virus E or truncated JEV E, were protected against subsequent viral challenges. The increased immunogenicity in the mice correlated with the increase in antibodies production. Moreover, the passive transfer of sera from immunized mice conferred protection against viral challenge to the recipient mice. On the other hand, dengue type 4 50% E which was extracellulary secreted did not show an increase of immunogencity and protective efficacy. Accordingly, surface expression of the truncated form of the E protein appear responsible for the enhanced immunity.

Thus, the present invention further relates to vaccines for use in humans and animals such as pigs and horses against flavivirus infection. Protective antibodies against flaviviruses can be raised by administering a vaccine containing the recombinant virus of the present invention or the purified truncated E protein of the present invention. Vaccines of the present invention can also include effective amounts of immunological adjuvants known to enhance an immune response.

One vaccine of the present invention contains the recombinant vaccinia virus of the present invention, or its derivative using a strain of vaccinia virus certified for humans, in an amount sufficient to induce production of the encoded flavivirus E protein causing an immune response against flavivirus infection. The vaccine can be administer by an intradermal route.

Another vaccine of the present invention contains the truncated protein produced by host cells of the present invention, for example, Sf9 insect cells. As is customary for vaccines, the truncated E protein can be delivered in a pharmacologically acceptable vehicle to induce an antibody response. The truncated protein, preferably comprising between 80 and 81% of the N-terminus sequence, is expressed by the recombinant virus of the present invention (preferably, a recombinant baculovirus) during an infection by the recombinant virus and can be isolated from the cell lysate or the medium fluid using standard methods in the art.

The present inventors have shown that appropriately truncated E constructs of flaviviruses are candidate vaccines for the prevention of disease. Increased immunity has been exemplified with the use of truncated E of the dengue type 2, dengue type 4 and JEV flaviviruses. As one skilled in the art will appreciate, however, the results obtained with these examples can be extended to other flaviviruses. With the significant conservation of the E sequence among flaviviruses one skilled in the art can construct recombinant viruses which when used to infect host cells result in the production of highly immunogenic truncated E proteins. Such recombinant viruses or produced proteins can be used in vaccines to prevent associated viral diseases.

The following examples are given to further illustrate the preferred embodiments of the present invention without being deemed limitative thereof. In particular, the following examples relate to dengue type 4 and type 2 viruses and Japanese encephalitis virus. However, other flaviviruses can be manipulated in similar ways to produce a more highly antigenic protein for use in vaccines.

EXAMPLES

Materials and Methods

The following materials and methods were utilized throughout the examples.

Dengue Virus Experiments (1). Construction of dengue virus DNA's coding for full-length and C-terminally truncated E's.

The dengue virus cDNA fragment that codes for the putative 15 amino acid N-terminal signal and the entire E sequence except the last 39 amino acids at the C-terminus was obtained earlier (Bray, M., B. Zhao, L. Markoff, K. H. Eckels, R. M. Chanock, and C. -J. Lai. 1989. Mice immunized with recombinant vaccinia virus expressing dengue 4 virus structural proteins with or without nonstructural protein NS1 are protected against fatal dengue virus encephalitis. J. Virol. 63:2853–2856). An extended DNA fragment coding for the N-terminal signal, the entire E plus the first 30 amino acids of the downstream NS1 nonstructural protein was constructed from the previously derived DNA fragment terminating at the Sst I site at nucleotide 1931 of the dengue type 4 viral sequence and the Sst I - Sau 3A DNA fragment (nucleotides 1931–2592) using the shared Sst I site for joining. This extended E DNA construct was inserted into the Bgl II site of intermediate vaccinia vector plasmid pSC11 (Chakrabarti, S., K. Brechling, and B. Moss. 1985. Vaccinia virus expression vector: coexpression of β-galactosidase provides visual screening of recombinant virus plaques. Mol. Cell. Biol. 5:3403–3409; and Falgout, B., R. M. Chanock, and C. -J. Lai. 1989. Proper processing of dengue virus nonstructural glycoprotein NS1 requires the N-terminal hydrophobic signal sequence and the downstream nonstructural protein NS2A. J. Virol. 63:1852–1860). At the downstream Bgl II site regenerated in the recombinant DNA construct a linker sequence was inserted consisting of oligo 2196 (GATCCTAGCTAGCTAGGTACC) (SEQ. ID. NO:1) and oligo 2197 (GATCGGTACCTAGCTAGCTAG) (SEQ. ID. NO:2) that contained stop codons in all three reading frames followed by a Kpn I cleavage site. The insertion of this linker sequence destroyed the joining Bgl II site leaving the unique upstream Bgl II site in the recombinant plasmid In order to obtain a library of DNA fragments specifying full-length E and a series of C-terminally truncated E's, the extended DNA sequences cleaved from the plasmid by Bgl II and Kpn1 were digested with Bal 31 and the progressively shortened DNA fragments were ligated to a second Kpn 1 linker sequence consisting of oligo 2246 (TGAATGAATGAGATCTGGTAC) (SEQ. ID. NO:3) and oligo 2247 (CAGATCTCATTCATTCA) (SEQ. ID. NO:4) that contained stop codons in all three reading frames. After digestion with Bst EII at nucleotide 1438 of the dengue sequence, DNA fragments of various lengths were separated on agarose gel and isolated for replacement of the extended DNA region between Bst EII and Kpn I in pSC11-E DNA. This procedure allowed construction of DNA coding for 40% to 100% of the E sequence. Recombinant 100*% E contained full-length E plus 4 N-terminal amino acids of the downstream NS1 nonstructural protein, while recombinant 100**% E contained full-length E plus the N-terminal 22 amino acids of the NS1 sequence. A similar scheme was employed to construct other shorter E DNA's. In these instances, Bst E II linearized DNA was the starting material for digestion by Bal 31. The precise deletion junctions of each of these DNA constructs were determined using oligo 1852 (CGTTTGCCATACGCTCACAG) (SEQ. ID. NO:5) located downstream of the DNA insert and within the pSC11 sequence as a negative strand primer in a dideoxynucleotide sequencing reaction (Sequencing system purchased from Promega Corporation).

DNA coding for a truncated E terminating at a specific amino acid residue such as 79% E plus -R, -RK, -RKG, -RKGS, or -RKGSS, was constructed using the polymerase chain reaction (PCR). The sequences used for the negative strand primers in the PCR were as follows:

79% E-RKGSS, oligo 2552
(AGATCTGGTACCTAGGAACTCCCTTTCCTGAA)
(SEQ. ID. NO:6);

79% E-RKGS, oligo 2553
(AGATCTGGTACCTAACTCCCTTTCCTGAACCA)
(SEQ. ID. NO:7);

79% E-RKG, oligo 2554
(AGATCTGGTACCTACCCTTTCCTGAACCAATG)
(SEQ. ID. NO:8);

79% E-RK, oligo 2647
(AGATCTGGTACCTATTTCCTGAACCAATGGAG)
(SEQ. ID. NO:9);

79% E-R, oligo 2648
(AGATCTGGTACCTACCTGAACCAATGGAGTGT)
(SEQ. ID. NO:10).

oligo 1426 (GATCTATGACTGTCTTCTTTGTCCTAA) (SEQ. ID. NO:11) was used as the positive strand primer for all of these PCR products. The PCR products were cleaved with Bst EII and Kpn I prior to their insertion into pSC11.

(2). Construction of recombinant vaccinia viruses.

CV-1 and Human TK⁻143 cells were grown and propagated in minimum essential medium plus 10% fetal calf serum (MEM10). Wild type vaccinia virus strain WR was used and recombinant vaccinia viruses were constructed according to the procedure described earlier (Chakrabarti, S., K. Brechling, and B. Moss. 1985. Vaccinia virus expression vector: coexpression of β-galactosidase provides visual screening of recombinant virus plaques. Mol. Cell. Biol. 5:3403–3409; and Zhao, B., E. Mackow, A. Buckler-White, L. Markoff, R. M. Chanock, C. J. Lai, and Y. Makino. 1986. Cloning full-length dengue type 4 virus DNA sequences: analysis of genes coding for structural proteins. Virology 155:77–88). Recombinant vaccinia virus vSC8 that contained a lacZ gene insert was used as a control.

(3). Labeling infected cells and protein analysis.

Infection of CV-1 cells with recombinant vaccinia viruses was essentially the same as detailed earlier (Bray, M., B. Zhao, L. Markoff, K. H,. Eckels, R. M. Chanock, and C. -J. Lai. 1989. Mice immunized with recombinant vaccinia virus expressing dengue 4 virus structural proteins with or without nonstructural protein NS1 are protected against fatal dengue virus encephalitis. J. Virol 63:2853–2856; and Zhao, B., E. Mackow, A. Buckler-White, L. Markoff, R. M. Chanock, C. -J. Lai, and Y. Makino. 1986. Cloning full-length dengue type 4 virus DNA sequences: analysis of genes coding for structural proteins. Virology 155:77–88). Sixteen to 20 hr after infection, the medium for cells in a 6-well plate was replaced with methionine-free MEM2 and after 1 hr of incubation this medium was replaced with 0.75 ml methionine-free MEM2 containing 100 μCi $^{35}$S-methionine (specific activity >800 Ci/mmol; Amersham Corp.). After a 2 hr labeling period, cells were lysed in RIPA buffer (1% sodium deoxycholate, 1% Nonidet P40, 0.1% sodium dodecyl sulfate, 0.1M Tris hydrochloride, pH 7.5, 0.15M NaCl) and the lysate centrifuged in a microfuge to remove particulate cell debris. The supernatant of the labeled lysate was used for analysis of viral proteins by immunoprecipitation. Intracellular and secreted forms of the various E products were also analyzed using recombinant virus-infected cells that were labeled for 6 hr. Fluid medium of infected cell cultures was collected after the labeling period and analyzed directly by immunoprecipitation. Infected cells were disrupted in a volume of RIPA buffer equivalent to the volume of the fluid medium. Dengue hyperimmune mouse ascitic fluid (HMAF) prepared against dengue 4 virus strain 814669 was used at a dilution of 1:5 or 1:20 for immunoprecipitation of the labeled lysates. A rabbit anti-serum raised against a dengue type 4 virus E peptide (peptide 73, amino acids 259–272 of the E sequence) was also used at a dilution of 1:5 or 1:20 for immunoprecipitation. The immunoprecipitates collected on Pansorbin (Calbiochem-Boehringer) were subjected to further digestion with endoglycosidase F (endo F) or endoglycosidase H (endo H) (Boehringer-Mannheim, Biochemicals) or analyzed directly by electrophoretic separation on SDS-polyacrylamide gel (acrylamide: bis=60:1.6, 12%). Labeled protein bands were visualized by fluorography.

(4). Immunization of mice.

Induction of resistance to experimental dengue virus encephalitis was evaluated by infecting mice with a recombinant vaccinia virus and subsequently challenging these animals intracerebrally with 100 LD$_{50}$ of dengue type 4 virus strain H241 as described earlier (Bray, M., B. Zhao, L. Markoff, K. H,. Eckels, R. M. Chanock, and C. -J. Lai. 1989. Mice immunized with recombinant vaccinia virus expressing dengue 4 virus structural proteins with or without nonstructural protein NS1 are protected against fatal dengue virus encephalitis. J. Virol 63:2853–2856). Passive immunization was also evaluated using pooled sera from groups of mice immunized with recombinant vaccinia virus v(59% E), v(79% E-RKG), v(81% E), or v(100,% E). Five to six week old female BALB/c mice were each inoculated with a 0.6 ml volume of pooled sera by the intraperitoneal route. The next day the inoculated mice were challenged intracerebrally with 100 LD$_{50}$ of dengue type 4 virus strain H241 and observed for symptoms of encephalitis and mortality as described (Falgout, B., M. Bray, J. J. Schlesinger, and C. -J. Lai 1990. Immunization of mice with recombinant vaccinia virus expressing authentic dengue virus nonstructural protein NS1 protects against lethal dengue encephalitis. J. Virol. 64: 4356–4363, 1990).

(5). Sero-analysis by radioimmunoprecipitation.

E-specific antibodies in individual or pooled sera of immunized mice were analyzed by immunoprecipitation of a $^{35}$S-labeled lysate of dengue virus infected LLCMK$_2$ cells as described previously (Zhang, Y. M., E. P. Hayes, T. C. McCarty, D. R. Dubois, P. L. Summers, K. H. Eckels, R. M. Chanock, and C. -J. Lai. 1988. Immunization of mice with dengue structural proteins and nonstructural protein NS1 expressed by baculovirus recombinant induces resistance to dengue encephalitis. J. Virol. 62:3027–3031).

(6). Indirect immunofluorescence assay.

Confluent CV-1 cells in a chamber slide were infected with recombinant virus at a low multiplicity (less than 10 pfu/well). Sixteen to 24 hr after infection, cells were rinsed with minimum essential medium (MEM) and fixed with cold acetone (fixed cells). Alternatively, cells were rinsed with MEM but not treated with acetone (live cells) and were examined for cell surface expression of E. HMAF was used at 1:100 dilution as the first antibody and fluorescein conjugated rabbit anti-mouse immunoglobulins (IgG+IgM) were used as the second antibody in an indirect immunofluorescence test. Stained cells were observed in a fluorescence microscope.

(7). Construction of baculovirus recombinant expressing 80% E of dengue type 2 or type 4 virus.

A high yielding baculovirus-insect cell system that had been studied earlier (Zhang, Y. M., E. P. Hayes, T. C. McCarty, D. R. Dubois, P. L. Summers, K. H. Eckels, R. M. Chanock, and C.-J. Lai, 1988. Immunization of mice with dengue structural proteins and nonstructural protein NS1 expressed by baculovirus recombinant induces resistance to dengue encephalitis. J. Virol. 62:3027–3031)), was employed to produce the strategically engineered dengue virus E's. The dengue type 4 cDNA segment that codes for the 80% E was inserted into the baculovirus intermediate cloning vector, pVL941. Recombinant baculovirus expressing dengue type 4 80% E was constructed and isolated by serial dilution and selection of the desired polyhedrin-negative plaques conducted. Since dengue type 2 80% E was shown to be more immunogenic than the full length E, recombinant baculovirus expressing dengue type 2 80% E was similarly constructed. These recombinant baculoviruses were designated b(DEN4, 80% E) andb(DEN2, 80% E), respectively.

FIG. 9 shows the alignment of the 26 amino acid-sequence (positions 373–398) of dengue type 4 E glycoprotein with the corresponding sequences of three other dengue serotype E glycoproteins. Arg at position 392 of dengue type E has been shown to be critical for the antigenic structure. A conserved amino acid found dengue type 4 and a given dengue serotype is indicated by a dot.

(8) Analysis of extracellularly secreted dengue virus 80% E expressed by recombinant baculovirus.

To examine the synthesis and extracellular secretion of baculovirus expressed dengue virus 80% E, insect sf9 cells were infected with recombinant baculovirus b(DEN4, 80% E) or b(DEN2, 80% E). Two days after infection, the sf9 cells were radio-labeled for 2 hr and the labeling medium replaced with serum-free Grace medium (GIBCO Laboratories, Grand Island, N.Y.). Culture fluid was sampled at various times to determine the amount of the E product secreted relative to that detected in the cell lysate.

Figure 10:
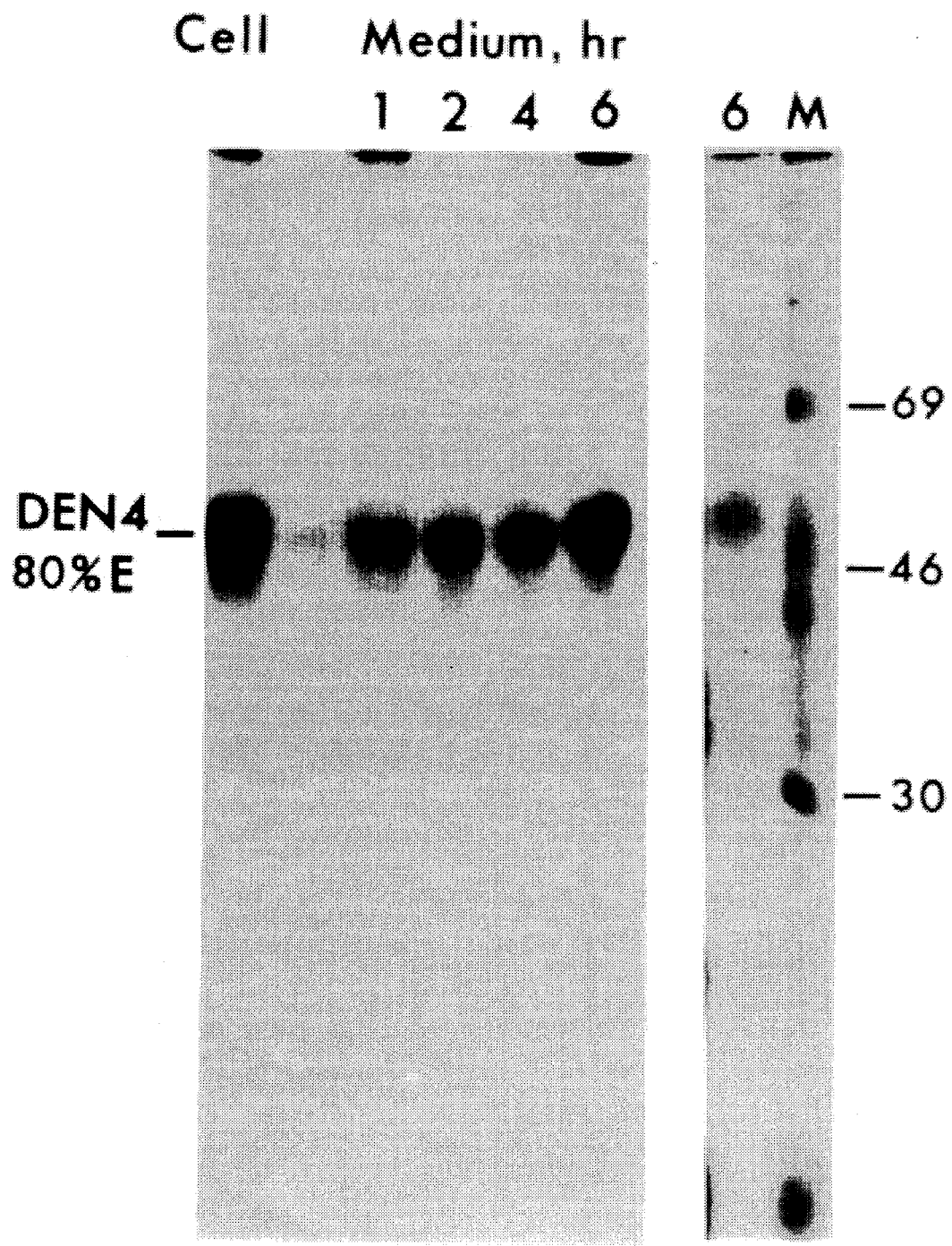
FIG. 10 shows the analysis of dengue type 4 virus 80% E expressed by recombinant baculovirus. Insect SF9 cells infected with recombinant baculovirus were radio-labeled for 2 hours and the labeling medium was replaced with serum-free Grace medium. Aliquots of the medium fluid were collected at various times for immunoprecipitation of extracellular 80% E. An equivalent aliquot of the cell update was also immunoprecipitated to determine the amount of 80% E that remained intracellularly. The six-hour medium sample was also analyzed without immunoprecipitation. The molecular weight markers (lane M) are shown on the right.

As shown in FIG. 10, dengue virus type 4 80% E detected in the medium increased with time during the 6-hr chase period. At six hours following the labeling, approximately 40% of the labeled E product was found in the medium. The secreted E product appeared to represent the major protein component in the medium as shown in the gel lane (far right) in which the fluid sample was not immunoprecipitated. This finding indicates that a significant fraction of baculovirus-expressed dengue type 4 virus 80% E is secreted extracellularly.

Japanese Encephalitis Virus (JEV) Experiments (9). Construction of recombinant plasmid containing JEV E cDNA.

JEV strain SA-14 was used as the challenge virus in the studies. A seed stock of JEV SA-14 challenge virus was prepared from the brain homogenate after two passages in suckling mouse brains. JEV JAOArS982 was used as the source for cDNA needed to construct the recombinant virus.

Polymerase chain reaction (PCR) was performed to derive appropriate JE virus cDNA fragments for expression by recombinant vaccinia virus. Briefly, template DNA was clone S-22 that was used to obtain the coding sequence for PreM, E and portions of flanking C and NS1 (Sumiyoshi, H., C. Mori, I. Fuke, K. Morita, S. Kuhara, J. Kundou, Y. Kikuchi, H. Nagamatsu, and A. Igarashi. 1987. Complete necleotide sequence of the Japanese encephalitis virus genome RNA. Virology 161:497– 510)). To construct the DNA fragment for expression of the full-length JEV E by PCR the positive strand primer was oligonucleotide (oligo) AAC AAC GGA TCC ATG GTG GTG TTT ACC ATC CTC CTG (SEQ. ID. NO:12). The primer introduces the flanking Bam HI cleavage sequence, an initiation codon preceding the coding sequence for the 15 amino acid hydrophobic signal preceding the N-terminus of E. The negative strand primer was oligo CAC ATG GAT CCT AAG CAT GCA CAT TGG TCG CTA A (SEQ. ID. NO:13) which provides the Bam HI sequence and a translation stop following the last coding sequence of E.

The JEV DNA fragment coding from the 80% E was constructed using the same positive strand primer as shown above and oligo GCC TAG GGA TCC TCA AGC TTT GTG CCA ATG GTG GTT (SEQ. ID. NO:14) was the negative strand primer. This negative strand primer contains a stop codon and the Bam HI cleavage sequence following the coding sequence for alanine at position 399. Both predicted PCR products were isolated after separation on an agarose gel, cleaved by Bam HI digestion, and inserted into the intermediate transfer vector pSC11 (Bgl II). The structures of both recombinant DNA constructs were verified by sequencing across the Bam HI-Bgl II junctions.

(10). Recombinant Vaccinia Virus containing JEV E and analysis of radio-labeled proteins.

The procedure used for construction of recombinant vaccinia virus from vaccinia virus WR and pSC11 derivatives was essentially as described above. CV-1 cells and TK⁻43 cells were grown in Eagle's minimum essential medium containing 10% fetal bovine serum. Recombinant virus was plaque-purified and the grown virus stock titered on CV-1 monolayers. Radio-labeling of recombinant virus infected cells was performed according to the method described in Section (3), Materials and Methods hereinabove.

Briefly, CV-1 cells were infected with recombinant vaccinia virus at an m.o.i. of 2–5 pfu/cell. Fifteen to twenty hours after infection, cell medium was removed and the cells placed in methionine free MEM for 1 hr and then in the same medium containing $^{35}$S-methionine (specific activity about 800 Ci/mmole) for 2 hr. Labeled cells were lysed in RIPA buffer not needed (components described on p.25) and the lysate prepared for immunoprecipitation using JEV hyperimmune ascitic fluid (HMAF) (American Type Culture Collection, Rockville, Md.).

To analyze JEV E on the infected cell surface, radiolabeled cells in a 6-well plate were placed in 0.5 ml MEM containing HMAF at 1:100 dilution for 1 hr at 37° C. After extensive washing with MEM to remove excess HMAF that was not bound to E on the cell surface or remained in the medium, cells were lysed in RIPA buffer (1% sodium deoxycholate, 1% Nonidet P40, 0.1% sodium dodecyl sulfate, 0.1M Tris hydrochloride, pH 7.5, 0.15M NaCl) and the lysate used directly for precipitation with Pansorbin beads (Calbiochem-Boehringer). The medium fraction collected following the labeling period was made into RIPA buffer and analyzed by precipitation with JEV HMAF. Endogylcosidase F (Endo F), or endogylcosidase H (Endo H) (Boehringer-Manheim Biochemicals) was used for digestion of the immunoprecipitates as suggested by the manufacturer. All immunoprecipitates were collected on Pansorbin and analyzed on SDS-12% polyacrylamide gels (acrylamide-:bis=60:1.6). Fluorography was performed to reveal the labeled proteins on the gel.

(11). JEV immunization and challenge.

In the protection study, 3 week-old female mice outbred strain CD-1 were inoculated at an intraperitoneal site with $3\times10^6$pfu of recombinant vaccinia virus expressing JEV E described above. The mice were again inoculated 14 days later. One week after the second inoculation, mice were bled and the following day challenged intraperitoneally with 100 $LD_{50}$ of JE virus SA-14 in 0.3 ml. As part of the challenge, mice were also intracerebrally inoculated with 0.03 ml virus-free MEM. JEV infected mice were observed for symptoms of viral encephalitis and death daily for 3 weeks. Control mice were immunized with recombinant vaccinia virus vSC8. In the immunogenicity study, three inbred strains of mice (BALB/c, C57BL/6, and C3H/He) at 3 weeks of age were immunized intraperitoneally twice with $3\times10^6$pfu/dose of recombinant vaccinia virus at 14 day intervals. Blood samples collected one week after the second inoculation.

(12). Analysis of sera using radioimmumnoprecipitation and ELISA.

For radioimmunoprecipitation, JE SA-14 virus-infected cells labeled with $^{35}S$-methionine were lysed and the lysate was used as the labeled antigen. 3 μl of individual or pooled mouse sera was added to 20 μl of the labeled lysate and the mixture incubated on ice for 2 hr. The immunoprecipitate was analyzed on polyacrylamide gels as described above.

For the ELISA, the antigen in the solid phase was sucrose gradient-purified JEV SA-14 virus, and the second antibody was peroxidase-conjugated goat anti-mouse IgG (Kirkegaard and Perry Laboraties, Gaithersburg, Md.). Sera at 1:1000 dilution was the starting concentration and serially two-fold diluted for testing.

Results (1). Synthesis of C-terminally truncated dengue E glycoproteins.

In an earlier study it was shown that recombinant vaccinia virus expressing the N-terminal 93% sequence of dengue E induced complete protection in mice similar to that afforded by recombinant vaccinia virus expressing the full-length dengue E and NS1 glycoproteins. This observation confirmed the importance of E as an independent protective antigen. For this reason, efforts were initiated to identify the regions of the E glycoprotein involved in stimulating protective immunity. Initially, cDNAs coding for C-terminally truncated E of varying length were constructed and the expressed products were analyzed for their ability to bind dengue type 4 virus hyperimmune ascitic fluid (HMAF). Because the polyclonal antibodies present in HMAF were raised against full-length intact E, it was expected that these antibodies should react with a wide variety of linear as well as conformational antigenic determinants that are normally present on E.

As described above in Materials and Methods, recombinant DNA's coding for the full-length E (100%), or 99%, 94%, 88%, 81%, 79%, 70%, 66%, 59%, 50%, 37%, 27%, 19%, or 9% of the N-terminal sequence of E were constructed. Each recombinant plasmid was sequenced to determine the truncation site in order to identify the sequence coding for the C-terminal amino acids of the E product. The predicted C-terminal amino acid sequences are shown below in Table I.

TABLE I

Predicted amino acids of C-terminally truncated dengue envelope glycoproteins expressed by recombinant vaccinia viruses

| Recombinant (% E expressed) | Predicted amino acids |
|---|---|
| v (9% E) | $M_1—D_{42}$ |
| v (19% E) | $M_1—C_{92}\underline{LNE}$ |
| v (27% E) | $M_1—L_{135}\underline{DE}$ |
| v (37% E) | $M_1—T_{182}\underline{LNE}$ |
| v (50% E) | $M_1—A_{245}$ |
| v (59% E) | $M_1—E_{290}\underline{NE}$ |
| v (66% E) | $M_1—E_{327}\underline{GE}$ |
| v (70% E) | $M_1—K_{344}\underline{DE}$ |
| v (79% E) | $M_1—F_{391}\underline{E}$ |
| v (81% E) | $M_1—K_{399}\underline{MNE}$ |
| v (88% E) | $M_1—H_{436}\underline{E}$ |
| v (94% E) | $M_1—W_{464}\underline{MNE}$ |
| v (99% E) | $M_1—G_{489}$ |
| v (100*% E) | $M_1—A_{494}\underline{DMGC}$ |
| v (100**% E) | $M_1—A_{494}\underline{D_1—V_{22}}$ |

Recombinant vaccinia viruses containing this series of E DNA's were then constructed and used for infection of CV-1 cells. $^{35}S$-methionine labeled lysates were prepared from infected cells, precipitated with HMAF, and the precipitates analyzed by polyacrylamide gel electrophoresis. Each of the eight recombinants that contained 59% or more of the coding sequence produced a dengue E specific protein of the predicted size (see FIG. 1). Digestion with endoglycosidase F reduced the molecular size of each product to the value estimated for the unglycosylated protein. The products of recombinants v(100*% E) and v(100**% E), each containing the full-length E plus additional NS1 sequences, were similar in size to the product of v(99% E) suggesting the additional NS1 sequences were proteolytically cleaved from the full-length E product. The gel mobility of 88% E was similar to that of the full-length E. The reason for abnormal gel migration of E's larger than 88%, including the 93% E described in an earlier study, was not clear (Bray, M., B. Zhao, L. Markoff, K. H. Eckels, R. M. Chanock, and C. -J. Lai. 1989. Mice immunized with recombinant vaccinia virus expressing dengue 4 virus structural proteins with or without nonstructural protein NS1 are protected against fatal dengue virus encephalitis. J. Virol. 63:2853–2856). The most interesting observation was that dengue E that was 81% or longer was detected with similar high efficiency and this level was significantly higher than that detected for 79% E or other smaller E products. 50% E was very weakly immunoprecipitated by HMAF and so were other smaller E's not shown in FIG. 1. The reduced detection of these E's was not due to incomplete immunoprecipitation since a three-fold increase of HMAF failed to precipitate more labeled E product.

(2). Detection of C-terminally truncated E's by an anti-peptide serum.

Figure 2:
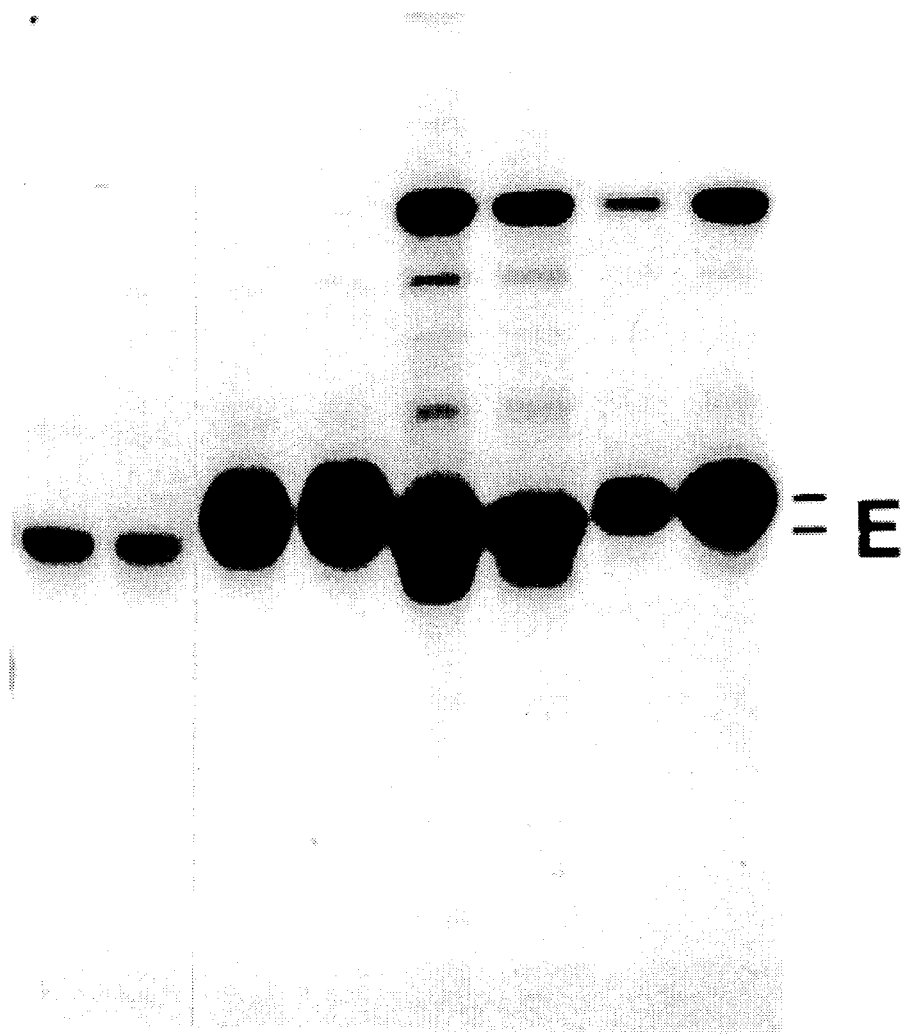
FIG. 2 demonstrates the differential HMAF binding affinities of two truncated dengue E's. The labeled lysates of cells infected with recombinants v(79% E) and v(81% E) were the same as described in FIG. 1. Each lysate was divided into four equal aliquots: two were precipitated with HMAF in one- and three-fold concentrations. The other two precipitated with a rabbit anti-peptide serum directed against peptide 73 of the E protein (amino acid 259–272) also in one- and three-fold concentrations. E-specific protein bands are indicated. Other bands labeled present in the high molecular weight region in the precipitates with the rabbit serum, were apparently not related to dengue E.

It was possible that the reduced level of detection of 79% E or other smaller E species was because these shortened E's were unstable following synthesis and therefore accumulated to a lower concentration within infected cells. This does not appear to be the case for 79% E, 70% E, 66% E, or 59% E as indicated by an experiment using an anti-serum prepared in rabbits against a 14-amino acid peptide of E (peptide 73, amino acids 259–272 of E) for immunoprecipitation of the radio-labeled E products (Markoff, L. J., M. Bray, C. -J. Lai, R. M. Chanock, K. Eckels, P. Summers, M. K. Gentry, R. A. Houghton, and R. A. Lerner. 1988. Antigenic analysis of the dengue virus envelope glycoprotein using synthetic peptides, pp. 161–165. In H. Ginsberg, F. Brown, R. A. Lerner, and R. M. Chanock (ed.), Vaccines 88: New chemical and genetic approaches to Vaccination. Cold Spring Harbor Laboratory, Cold Spring Harbor, N.Y.). The sequence of this peptide is located 55% from the N-terminus of E. HMAF detected 81% E at a high level but 79% E at a much lower level. On the other hand, peptide 73 antiserum precipitated both E's to the same extent suggesting that 79% E, was as stable as 81% E, but was not precipitated efficiently by HMAF (see FIG. 2). Similarly, an increased level of detection by peptide 73 antiserum was observed for 70%, 66%, or 59% E. Peptide 73 antiserum did not precipitate 50% E or other smaller E species lacking the peptide sequence. The finding that the binding of HMAF was similar for E's ranging from 81% to the full-length but significantly reduced by an additional 2% C-terminal deletion of E (ie, 79% E), suggested that the sequence 2% upstream of the C-terminus of 81% E acts to maintain the configuration of E required for major conformational epitopes of E recognized by HMAF.

(3). The E sequence critical for binding HMAF.

Because 79% E and 81% E exhibited a marked difference in HMAF binding affinity, the extended C-terminal dengue 4 sequence of 8 amino acids, Arg(R)-Lys(K)-Gly(G)-Ser(S)-Ser(S)-Ile(I)-Gly(G)-Lys(K) (SEQ. ID. NO:15) present in 81% E was examined in an attempt to identify the precise amino acid sequence responsible for the abrupt transition of HMAF binding efficiency. Additional recombinants that extended the C-terminus of 79% E to include R, R-K, R-K-G, R-K-G-S, or R-K-G-S-S were constructed. HMAF efficiently precipitated 79% E-R, and also the other longer E species, but not 79% E. On the other hand, peptide 73 antiserum detected 79% E, 79% E-R, and other larger E products with similar efficiency (see FIG. 3).

Thus, the arginine residue immediately downstream of the C-terminus of 79% E is required for the formation and/or maintenance of the native conformation of E and thus conformational E epitopes recognized by HMAF. This further suggests that the arginine residue at position 392 plays a critical role in the proper folding of dengue E during or after polypeptide synthesis presumably through a charged amino acid interaction between this arginine and the other regions of the molecule.

Figure 3:
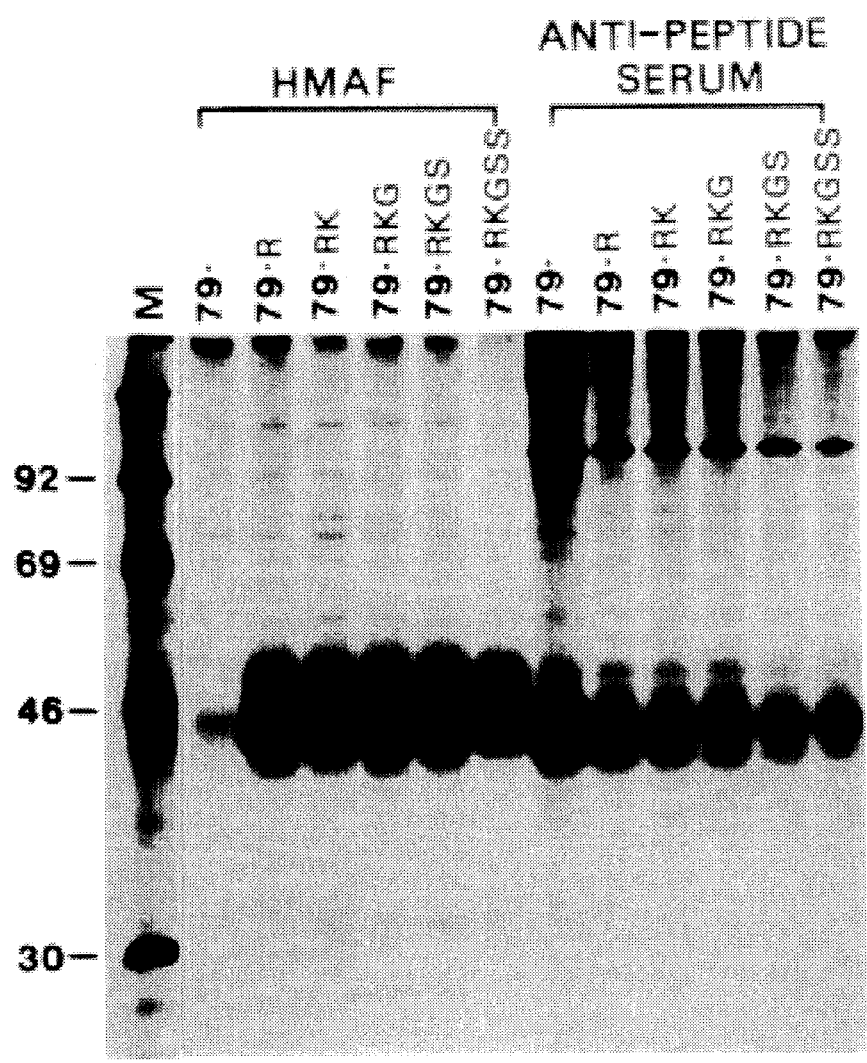
FIG. 3 shows the amino acid sequence involved in transition of dengue E antigenic structure. $^{35}$S-methionine labeled lysates were prepared from CV-1 cells infected with recombinant vaccinia viruses that expressed 79% E, 79% E-R, 79% E-RK, 79% E-RKG, 79% E-RKGS, and 79% E-RKGSS. Equal aliquots of each lysate were precipitated separately with HMAF and with rabbit anti-peptide 73 serum followed by analysis on SDS-polyacrylamide gel. M shows sizes of protein markers in kilodaltons.

This position in the linear E sequence appears to represent a transition between the two classes of E's that are distinguishable by their binding affinities to HMAF (FIG. 3). Since this arginine is located C-terminal of the last cysteine residue, it is likely that this charged amino acid influences the folding of the E molecule during nascent synthesis so that cysteine residues can be brought into close proximity for disulfide bond formation which is a prerequisite for maintenance of a stable configuration. Of interest, this arginine corresponds in position to the trypsin cleavage site of tick-born encephalitis virus E glycoprotein at position 395 suggesting that this residue in the native E structure is accessible to the enzyme (Mandl, C. W., F. Guirakhoo, H. Holzmann, F. X. Heinz, and C. Kunz. 1989. Antigenic structure of the flavivirus envelope protein E at the molecule level, using tick-borne encephalitis virus as a model. J. Virol 63:564–571).

(4). Detection of extracellularly secreted E.

One of the major goals in the development of dengue vaccines has been to increase the immunogenicity of the E glycoprotein. It was speculated that the poor immunogenicity of the full-length E expressed by v(C-M-E-NS1-NS2A) stemmed from the intracellular targeting of the E product. Earlier, DNA sequences were constructed that specified 93% E lacking the entire C-terminal hydrophobic sequence in an attempt to produce an "anchor minus" E so that the product would be secreted extracellularly and possibly exhibit increased immunogenicity. However, 93% E was not detected in the medium and it also failed to induce a detectable level of antibodies in immunized mice.

Figure 4A:
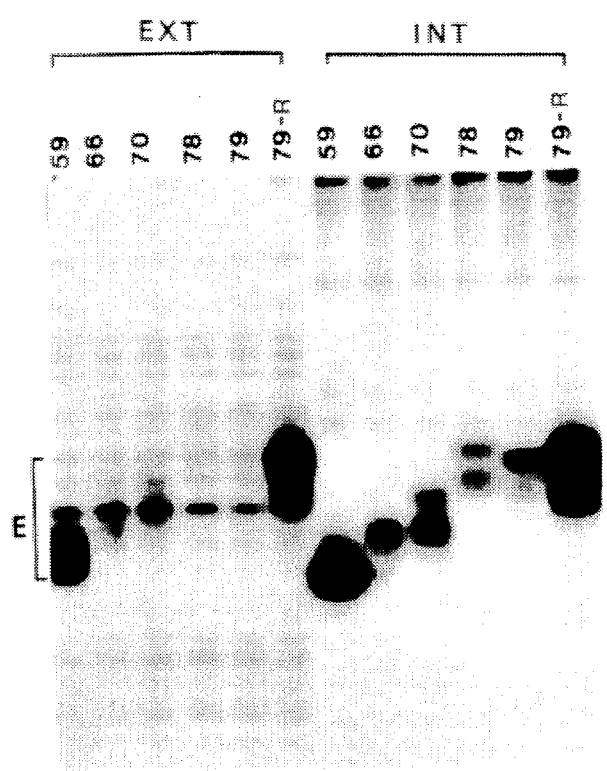
FIG. 4 shows an analysis of dengue E's in intracellular and extracellular fractions. CV-1 cells were infected with various recombinants expressing C-terminally truncated dengue E's of the sizes indicated, or were not infected (Mock). At 18 hours after infection, cells were labeled with $^{35}$S-methionine for 6 hours. The intracellular fraction (INT) and the extracellular (medium) fraction (EXT) were prepared and immunoprecipitated with HMAF for separation on SDS-polyacrylamide gel. Dengue E's in the gel lanes are indicated. The recombinant construct 100% E contained dengue DNA coding for the full-length dengue E plus 4 amino acids of NS1.
Figure 4B:
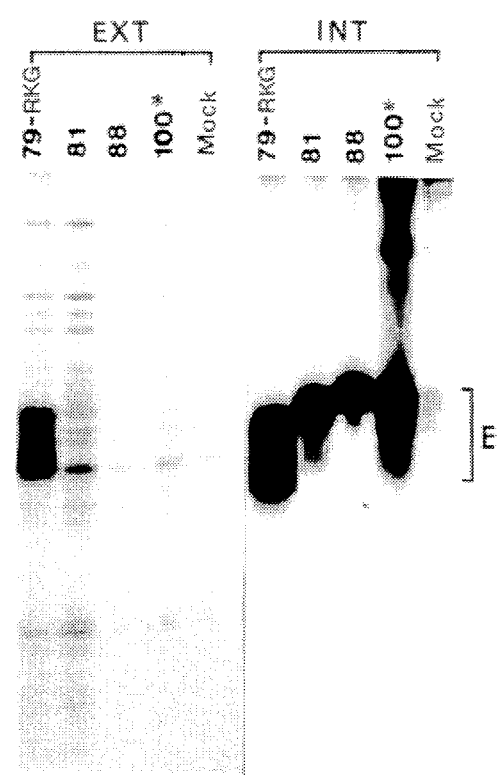
Figure 6A:
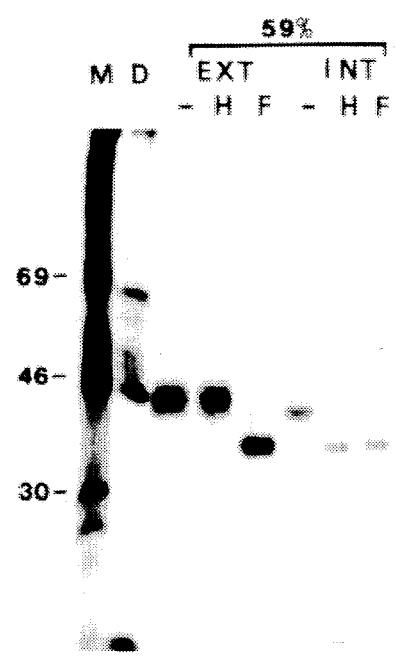
FIG. 6 shows an analysis of intracellular and secreted dengue E's by endoglycosidase digestion. Infection of CV-1 cells with recombinant viruses, radio-labeling, and immunoprecipitation were the same as described in FIG. 4. Immunoprecipitates were digested with endoglycosidase H (H), or endoglycosidase F (F), or mock-digested (−). The intracellular fraction (INT) or the extracellular fraction (EXT) of the recombinant E products was prepared for this analysis. M shows the molecular sizes of marker proteins in kilodaltons. D is the immunoprecipitate of dengue virus proteins for size comparison.
Figure 6B:
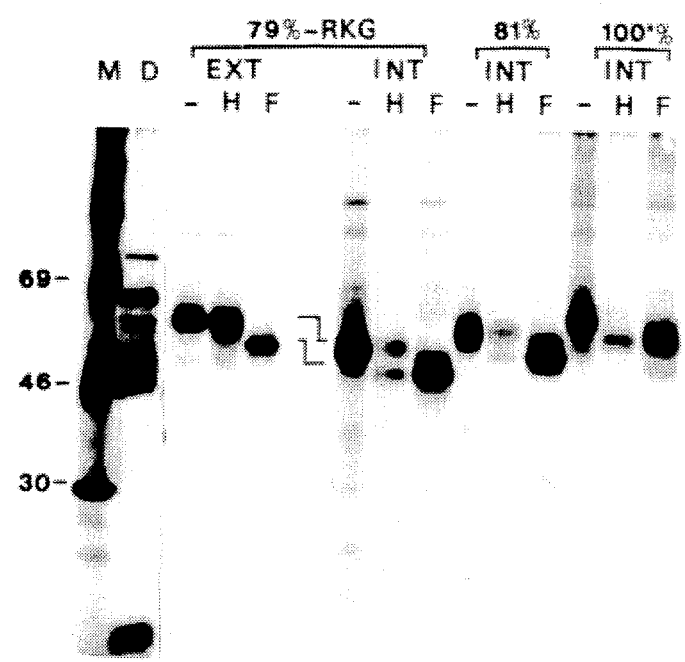

It was possible that sequences other than those present at the C-terminal hydrophobic region might be involved in the intracellular targeting of E. The series of E's that had sustained additional truncation at the C-terminus allowed the present inventors to determine if such specific targeting sequences had been removed allowing the resulting E's to be secreted extracellularly. CV-1 cells were infected with a recombinant expressing 59% E, 70% E, 79% E-R, 79% E-RKG, 81% E, 88% E, or 100% E. After a 6 hr period of labeling with $^{35}$S-methionine the cell lysate and the medium fractions were separately analyzed by immunoprecipitation with HMAF (see FIG. 4). HMAF detected the synthesis of each of the E's in the cell lysate fraction, although 79% E-R or 79% E-RKG and the three other larger E species were more efficiently precipitated than 79% E, or other smaller E's as observed earlier. 59% E, 66% E, 70% E, 79% E-R, and 79% E-RKG were detected in significant amount in the fluid medium ranging from 10–50% of the total labeled product. Similarly, 30–50% of label in 79% E-RK, 79% E-RKGS, or 79% E-RKGSS was also detected in the medium fraction during the 6 hr labeling period. Notably, 81% E that contains three amino acids Ile (I), Gly (G), and Lys (K) downstream of the C-terminus of 79% E-RKGSS was not secreted efficiently. Other E's larger than 81% were detected only in the cell fraction.

Since other longer E's were also not secreted, it appears that the three dengue C-terminal amino acids of 81% E (I-G-K) play a role in directing the intracellular distribution of E by preventing it from being exported and secreted. Deletion of these amino acids resulted in secretion of the E product. In addition to being secreted extracellularly, the series of five E's ranging in size from 79% E-R to 79% E-RKGSS as exemplified by 79% E-RKG was expressed in high concentration on the surface of recombinant virus-infected cells. This suggests that 79% E-RKG may be an integral membrane glycoprotein containing an anchor sequence for insertion into the cell membrane. Analysis of the C-terminal sequence suggested mechanism for insertion of this protein into the plasma membrane and secretion of a fraction of the protein extracellularly. There are 17 hydrophobic or neutral amino acids in a 20 amino acid stretch preceding the hydrophilic Arg-Lys-Gly sequence at the C-terminus. This hydrophobic structure resembles the C-terminal anchor of many surface glycoproteins in that a hydrophobic trans-membrane domain of length sufficient to span the lipid bilayer (usually 20–30 amino acids) is followed by a charged cytoplasmic domain of varying length.

It appears that this internal sequence of full-length E when it becomes external as a result of truncation of the C-terminus is able to function as a hydrophobic membrane anchor. The ability of the hydrophobic fusion-related external domain, which is also in an internal position of the simian virus 5 Fo precursor, to act as a stable membrane anchor has been described (Paterson, R. G., and R. Lamb. 11987. Ability of the hydrophobic fusion-related external domain of a paramyxovirus F protein to act as a membrane anchor. Cell 48:441–452). In that study the hydrophobic structure was placed at the C-terminus of an influenza virus hemagglutinin replacing the normal C-terminal anchor. A short cytoplasmic domain containing only three amino acids, Lys-Val-Lys, is found at the C-terminus of immunoglobulin μ and δ membrane heavy chains (Cheng, H. -L., F. R. Blattner, L. Fitzmaurice, J. F. Mushinski, and P. W. Tucker. 1982. Structures of genes for membrane and secreted murine IgD heavy chain. Nature (London) 296:410–415; and Kehry, M., S. Ewald, R. Douglas, C. Sibly, W. Raschke, D. Fambrough, and L. Hood. 1980. The immunoglobulin μ chains of membrane-bound and secreted IgM molecules differ in their C-terminal segments. Cell 1:393–406). Evidence is available that the 3 amino-acid sequence linked to the transmembrane domain of vesicular stomatitis virus G protein is sufficient to direct protein transport from the site of synthesis in the ER through the Golgi complex to the plasma membrane (Puddington, L., C. E. Machamen, and J. K. Rose. 1986. Cytoplasmic domains of cellular and viral integral membrane proteins substitute for the cytoplasmic domain of the vesicular stomatitis virus glycoprotein in transport to the plasma membrane. J. Cell. Biol. 102:2147– 2157). The sequence of 3 amino acids in the C-terminal domain of 79% E-RKG, or especially, the sequence of one charged amino acid (Arg) in the C-terminal domain of 79%-R is considerably shorter than the cytoplasmic domains of other viral integral membrane proteins and may affect its stable association with membranes as a similar finding has been described (Kilpatrick, D. R., R. V. Srinivas, E. B. Stephens, and R. W. Compans. 1987. Effects of deletion of the cytoplasmic domain upon surface expression and membrane stability of a viral envelope glycoprotein. J. Biol. Chem. 262:16116– 16121). Perhaps for this reason, 79% E-RKG or 79% E-R failed to become firmly anchored on the membrane and, as a consequence, a fraction of the expressed protein was secreted.

This initially suggested that an increase in length of the anchor domain and/or the number of amino acids in the cytoplasmic domain might provide a more stable membrane association and less extracellular secretion. Consistent with this notion is the observation that 81% E containing three additional amino acids I-G-K at the C-terminus of 79% E-RKGSS was not secreted. However, extending the length of the cytoplasmic tail did not appear to stabilize membrane association because 81% E accumulated less abundantly on the surface. The effect of extending the length of the hydrophobic domain near the C-terminus of 79% E-RKG is currently under investigation.

(5). Detection of truncated E's on the cell surface.

An indirect immunofluorescence assay was employed to determine if any of the truncated E's accumulated on the surface of recombinant virus infected cells. FIG. 5 shows the result of this assay for several representative recombinants including v(59% E) and v(79% E-RKG), that expressed extracellular E's, and v(81% E) and v(100*% E), whose E product was not secreted extracellularly. Live cell immunofluorescence tests indicated that the E product of v(79% E-RKG) was present in high concentration at the cell surface, whereas v(81% E) infected cells exhibited considerably less cell surface antigen. 79% E-R, 79% E-RK, 79% E-RKGS, and 79% E-RKGSS were also assayed and shown to express a high concentration of E at the surface of infected cells. Cells infected with v(59% E) or v(100*% E) were negative by this assay (see FIG. 5).

These observations indicate that the addition of an arginine-residue (position 392 of the E sequence) at the C-terminus of 79% E alters this molecule so that it becomes stably associated with the cell membrane and accumulates in high concentration at this site. As shown earlier, arginine at position 392 is also critical for the formation and maintenance of the native antigenic structure of E and for efficient secretion from recombinant virus infected cells. Although both 59% E and 79% E-RKG were secreted extracellularly only 79% E-RKG was detected on the cell surface. On the other hand, 81% E accumulated in low concentration on the cell surface but was not secreted. Finally, 100% E was detected only inside recombinant virus infected cells. Of particular interest was the finding that a high level of 79% E-RKG was detected extracellularly as well as on the cell surface. Although the available evidence suggests that these truncated dengue E glycoproteins are retained in the plasma membrane by a C-terminal anchor structure, the exact mechanisms by which 79% E-RKG is anchored on the cell membrane and is also secreted extracellularly remain to be elucidated.

(6). Endoglycosidase analysis of intracellular and extracellular E's.

In order to determine whether extracellular E's were secreted by a protein export pathway or were released during cell lysis at a late stage of virus infection, both extracellular and intracellular E's were subjected to endoglycosidase digestion. The intracellular fraction of 59% E was sensitive to digestion by endo H or endo F indicating that its carbohydrate moiety was of the mannose-rich type that is added during the first stage of glycosylation during protein synthesis (see FIG. 6). On the other hand, extracellular 59% E was completely resistant to endo H digestion. This indicates that 59% E had entered the secretory pathway through the Golgi apparatus where endo H-resistant carbohydrates were added prior to secretion into the medium. FIG. 6 also shows that the extracellular 79% E-RKG, similar to extracellular 59% E, was completely resistant to endo H, whereas the intracellular form of 79% E-RKG was partially sensitive to endo H. In contrast, intracellular full-length E was completely sensitive to endo H digestion. This indicates that secreted 79% E-RKG expressed by the recombinant virus had also undergone further modification of its carbohydrate side chains. Since such modifications normally occur in the Golgi apparatus in the protein transport pathway for most surface glycoproteins and secretory glycoproteins, it appears that both C-terminally truncated 59% E and 79% E-RKG enter into the export pathway but this pathway is not taken by full-length E. In the case of 81% E, the intracellular form contained both endo H sensitive and endo H resistant carbohydrate moieties similar to those found for intracellular 79% E-RKG. This finding suggests that 81% E was also directed in part into the export/secretory pathway consistent with the previous observation that a small fraction of this protein was detected on the cell surface. It is interesting to note that despite the similarity of glycosylation pattern, 81% E accumulated to a lesser extent on the cell surface than did 79% E-RKG. 81% E also failed to be secreted extracellularly.

(7). Protective immunity induced by C-terminally truncated E's.

The protective efficacy of 15 recombinant vaccinia viruses that expressed full-length E or C-terminally truncated dengue E ranging from 9% to 99% of the colinear N-terminal sequence was evaluated by challenging immunized mice with dengue type 4 virus intracerebrally. A summary of 4 separate immunization-challenge studies is presented in FIG. 7. The protection rate, shown as percent survival, represents the number of survivors relative to the number of immunized mice.

Mice immunized with v(79% E-RKG) or with a recombinant expressing 81%, 88%, 94%, 99%, or 100% E were completely protected or almost completely protected against dengue virus challenge, ie., overall protection rates of 94–100%. On the other hand, mice immunized with v(79% E), or a recombinant expressing a smaller product (ie., 70%, 66%, 59%, 50%, 37%, 27%, or 19% E) were partially protected (40–78% over-all protection rate) with the exception of v(59% E) which consistently gave a high protection rate (9/10, 9/10, 6/7 in separate experiments) against dengue virus challenge. Significant resistance induced by 19% E indicates that at least one protective antigenic site is located within the first 92 amino acids of E. v(9% E) had the lowest protection rate (17%) which was similar to the value observed for the control recombinant vSC8. An interesting correlation became apparent when the protection rate and HMAF binding affinity were compared. Recombinant E's that induced the highest level of resistance to dengue virus encephalitis also exhibited high HMAF binding affinity suggesting that mature conformational structure of the dengue E glycoprotein is an important factor in inducing effective protective immunity.

In this regard, it appears that 59% E displays one or more major protective antigenic sites and one such site is located within the first 19% of the N-terminal sequence of E, ie, the N-terminal 92 amino acids of E since immunization with v(19% E) induced a significant protein against dengue encephalitis. Mapping of antigenic sites on Murray Valley encephalitis virus (MVE) E glycoprotein has been studied recently using a series of synthetic peptides for immunization (Roehrig, J. T., A. R. Hunt, A. J. and J. H. Matthews. 1989. Synthetic peptide vaccine strategy for inducing flavivirus immunity. In vaccines 89: Modern Approaches to New Vaccines Including Prevention of AIDS. R. A. Lerner, H. Ginsberg, R. M. Chanock, and F. Brown, (ed.), pp. 347–350. Cold Spring Harbor Laboratory). The results showed that amino acids 35–50 of the MVE E sequence induce neutralizing antibodies and protection in immunized mice. It is interesting to note that this sequence is also located within the first 19% of the N-terminal sequence.

(8). Antibody response of mice immunized with various vaccinia recombinant viruses expressing E of varying length.

Figure 8:
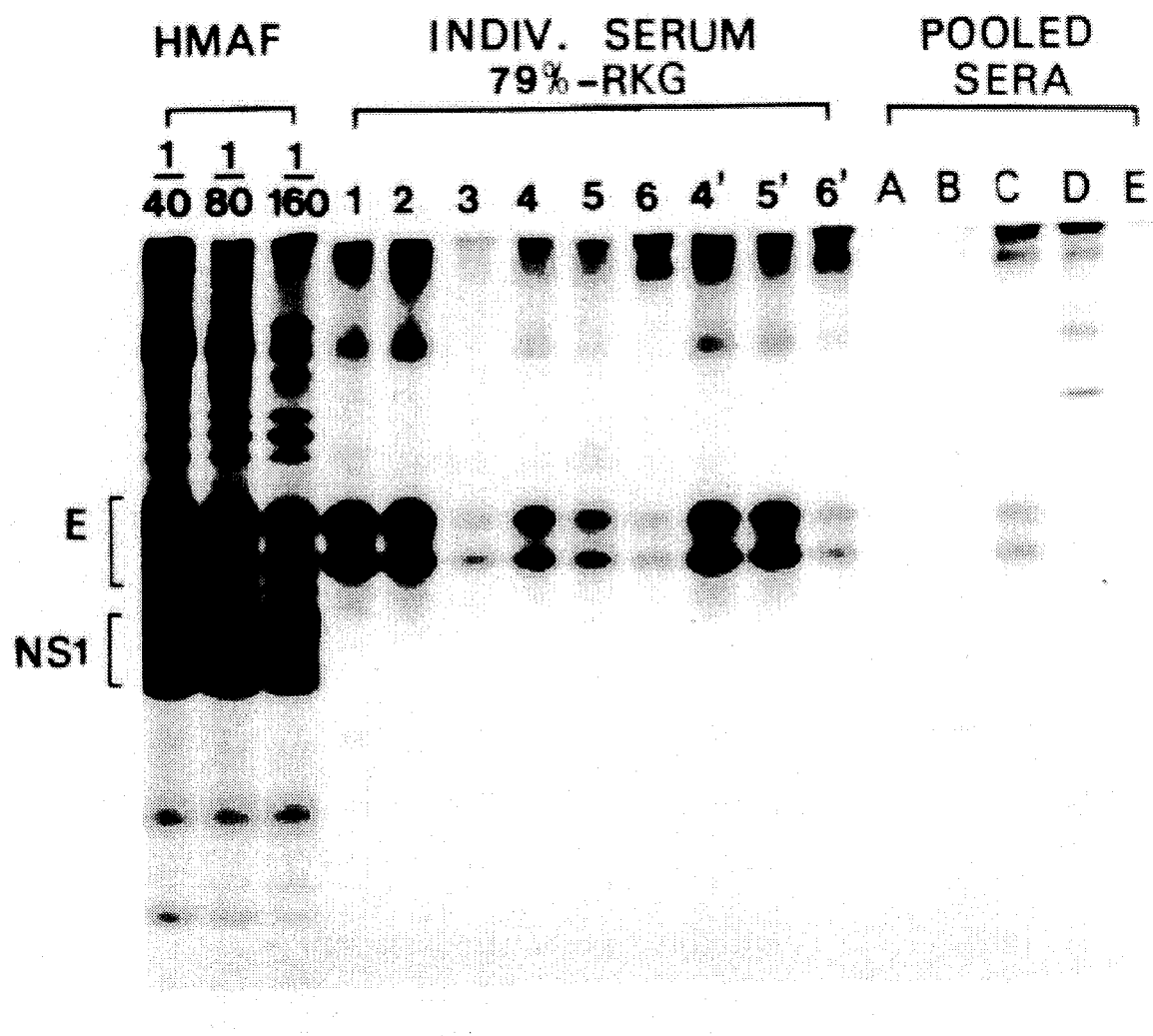
FIG. 8 shows an analysis of E antibodies in sera of immunized mice by radio-immuno precipitation. Lanes 1, 2, 3, 4, 5, and 6 are serum samples from individual mice immunized once with v(79% E-RKG). Lanes 4', 5' and 6' indicates serum samples collected from the same animals 5 days later. Lanes in the pooled sera are: A, mice infected with vSC8 (Control vaccinia virus); B, with v(59% E); C, with v(79% E-RKG); D, with v(81% E); and E, with v(100,% E). As a reference standard, HMAF at 1/40, 1/80, or 1/160 dilution was used for precipitation of the same labeled dengue antigen preparation.

The level of E specific antibodies in sera of immunized mice was analyzed by radio-immunoprecipitation to determine whether C-terminal truncation of E increased its immunogenicity. Individual sera from 3–5 mice in each group were initially tested. Groups of mice that were partially protected in the challenge studies failed to develop detectable E antibodies in response to immunization. In contrast, each of the mice immunized with v(79% E-RKG) developed a moderate to high level of E antibodies. However, not all groups of mice that exhibited complete or almost complete resistance to virus challenge developed such an E antibody response to immunization. For example, mice immunized with 81% E developed a low level of E antibodies while mice immunized with 100% E failed to develop detectable E antibodies (see FIG. 8). The level of E antibodies in individual sera of mice immunized with v(79% E-RKG) was equivalent to that present in a 1:80 to 1:160 dilution of HMAF as measured by immunoprecipitation. Thus, among the various truncated and full-length E constructs tested, 79% E-RKG was most immunogenic.

Pooled sera from mice immunized with v(100% E), v(81% E), v(79% E-RKG) and the vSC8 control were tested for dengue virus-neutralizing activities using the procedure of plaque-reduction neutralization test (Bancroft, W. H., J. M. McCown, P. M. Lago, W. E. Brandt, and P. K. Russell. 1979. Identification of dengue viruses from the Caribbean by plaque-reduction neutralization test. Pan Am. Health Rog. Sci. Publ. 375:175–178). The results showed that with sera raised against 79% E-RKG and 81% E the number of plaques was consistently lower than that of the vSC8 control although 50% plaque-reduction was not reached at 1:10 serum dilution.

Passive transfer of sera into mice followed by dengue virus challenge was also performed to determine whether serum antibodies induced by the various forms of E played a role in the resistance induced by immunization. As can be seen below in Table II, sera from mice immunized with v(79% E-RKG) or v(81% E) conferred on recipient mice solid protection against intracerebral dengue virus challenge. Sera from groups of mice immunized with v(100*% E) or with v(59% E) provided a somewhat lower passive protective effect (ie., 80% or 50% survival, respectively). In addition, morbidity was observed in these animals following dengue virus challenge, whereas this was not the case in mice passively protected by serum from mice immunized with 79% E-RKG or 81% E. It appears that E antibodies induced in mice following immunization with v(79% E-RKG), or v(81% E) played a major role in the resistance to lethal dengue virus challenge exhibited by these vaccinated animals.

TABLE II

Protection of mice against dengue virus challenge following passive transfer of sera from donor mice immunized with recombinant vaccinia virus expressing the full-length and C-terminally truncated E's

| Serum donor mice immunized with | Response to dengue challenge no. of mice that survived relative to no. of mice that received sera | Protection rate (%) |
| --- | --- | --- |
| v (100*% E) | 8/10 | 80 |
| v (81% E) | 10/10 | 100 |
| v (79% E-RKG) | 10/10 | 100 |

TABLE II-continued

Protection of mice against dengue virus challenge
following passive transfer of sera from donor mice
immunized with recombinant vaccinia virus expressing
the full-length and C-terminally truncated E's

| Serum donor mice immunized with | Response to dengue challenge no. of mice that survived relative to no. of mice that received sera | Protection rate (%) |
|---|---|---|
| v (59% E) | 5/10 | 50 |
| vSC8 | 1/10 | 10 |

Among the truncated E molecules that were able to bind antibodies in dengue virus HMAF efficiently, only 79% E-RKG was highly immunogenic when tested for induction of E antibodies. This truncated E was unique in being expressed in high concentration on the surface of infected cells. 79% E-RKG was also secreted extracellularly but other truncated E constructs that were also secreted efficiently did not induce a detectable E antibody response. This suggests that cell surface expression of 79% E-RKG was responsible for its enhanced immunogenicity. However, it is not possible to rule out the importance of a unique form of secreted E. The properties of 81% E were also consistent with the importance of cell surface expression of E in immunogenicity. There is evidence from studies with the S-antigen of *Plasmodium falciparum* that anchoring the secreted plasmodial antigen on the cell membrane increased immunogenicity several fold (Langford, C. J., S. J. Edwards, G. L. Smith, G. F. Mitchel, B. Moss, D. J. Kemp, and R. F. Anders. 1986. Anchoring a secreted plasmodium antigen on the surface of recombinant vaccinia virus-infected cells increases its immunogenicity. Mol. Cell. Biol. 6:3191–3199).

Thus, in addition to being more immunogenic than longer E constructs, 79% E-RKG and 81% E induced a higher level of resistance to experimental dengue virus disease.

(9). Immunization against dengue virus and other flaviviruses.

The observation that a C-terminally truncated dengue E glycoprotein containing approximately 80% N-terminal E sequence, that is expressed on the cell surface and secreted extracellularly, is more immunogenic and protective than full-length E may have implications for the development of effective vaccines for dengue virus disease as well as other flavivirus diseases. A truncated immunogenic E of dengue virus would also be more desirable than the full-length E if it lacked sequences responsible for inducing enhancing antibodies that have been suggested to play a role in the pathogenesis of dengue hemorrhagic fever/shock syndrome (Halsted, S. B. 1988. Pathogenesis of dengue: challenge to molecular biology. Science 239:476–481).

Appropriately truncated E constructs of other flaviviruses may also be suitable for the prevention of disease. There is significant conservation of E sequence among flaviviruses; amino acid homology among dengue viruses of different serotype ranges from 62 to 70% while homology among different flaviviruses ranges from 40–50%. Also, conservation of cysteine residues suggests conservation of the 3-dimensional structure of E. These similarities suggest that a strategic truncation at the C-terminus analogous to the 79% E-RKG of dengue type 4 virus may yield an E product that exhibits increased immunogenicity and protective efficacy.

The present inventors have recently evaluated the applicability of this strategy for another dengue virus serotype by constructing dengue type 2 virus (PR159, S1 strain) truncated E similar in size to 79% E-RKG of dengue type 4 virus. Immunization with the recombinant vaccinia virus expressing this C-terminally truncated E of dengue type 2 virus induced solid resistance in mice to challenge with type 2 virus. In contrast, immunization with a recombinant expressing the full-length E of dengue 2 virus induced only partial protection at a survival rate of less than 50% whereas unprotected animals all died following dengue challenge. This observation suggests that it may be possible to extend this strategy to construct highly immunogenic E glycoproteins of other flaviviruses, such as Japanese encephalitis virus and tick borne encephalitis virus that continue to threaten the public health.

(10). Comparison of sequences between dengue type 4 and Japanese encephalitis virus envelope glycoproteins.

As shown above, the C-terminally truncated dengue type 4 virus (DEN4) envelope (E) glycoprotein, approximately 80% in size, is more immunogenic than the full-length E in mice. Because of the conservation of the E sequence among flaviviruses, the truncation strategy was applied to improve the immunogenicity of the JEV E. Initially, the C-terminal sequence near the truncation site of dengue type 4 virus 80% E was compared with the corresponding sequence of JEV E. The 26 amino acid sequence at positions 373–398 of DEN4 E aligned with the JEV E sequence between amino acids 379–404 (FIG. 11). In this region, 13 amino acids were conserved between the two proteins. The antigenically critical Arg at position 392 of DEN4 E corresponded to Lys at position 398 of JEV E. Accordingly, a JEV E terminating at this position or plus one or more of the following four amino acids would exhibit increased immunogenicity.

To test the feasibility of the strategic truncation approach to improving the immunogenicity of JEV E, a JEV cDNA fragment that coded for the N-terminal 80% E terminating at Ala at position 399 was constructed. A cDNA fragment that codes for the full-length JEV E was also prepared. These DNA fragments were used to construct a recombinant vaccinia virus expressing the N-terminal 80% sequence of E designated v (JE, 80% E) or a recombinant vaccinia virus expressing the full-length E, designated v(JE, 100% E) as described above.

(11). Analysis of JEV E glycoprotein expressed by recombinant vaccinia virus.

Figure 12:
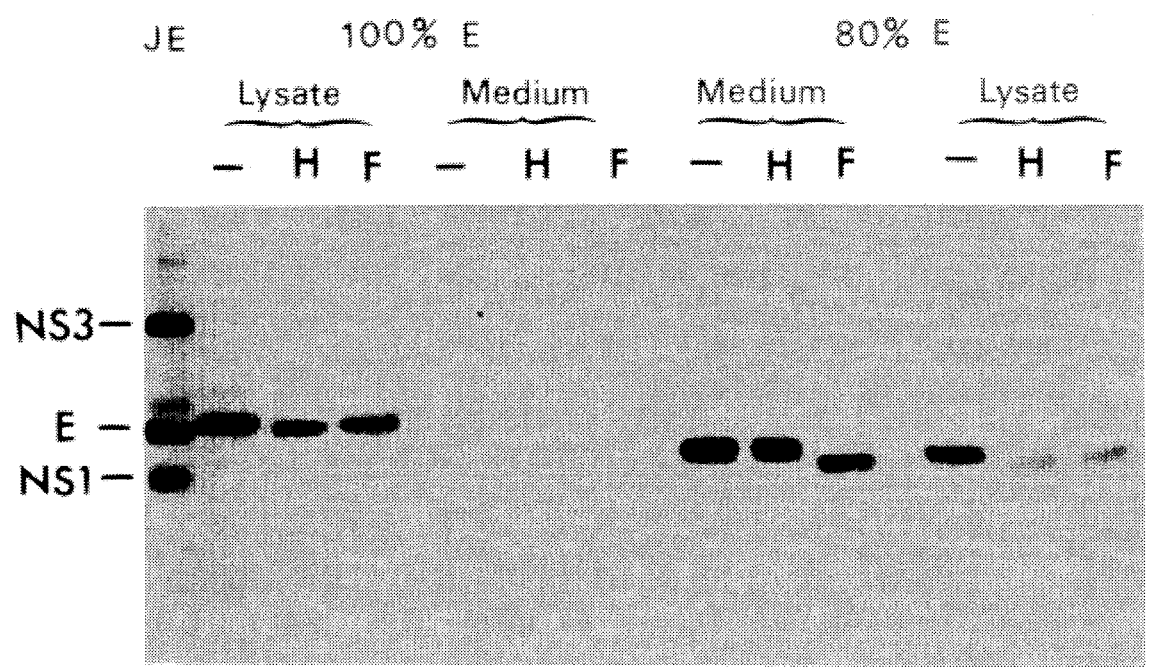
FIG. 12 Analysis of E glycoproteins expressed by recombinant vaccinia virus. CV-1 cells infected with recombinant v (JE, 100% E) or v (JE, 80% E) were labeled with $^{35}$S-methionine. At the end of labeling, the cell lysate was immunoprecipitated using JE HMAF. Both recombinant expressed E's were further digested with endo H (lane H) or endo F (lane F) to analyze the extent of glycosylation. The medium fraction of v (JE, 80%) or v (JE, 100%) infected cells was similarly analyzed. Marker proteins shown in lane JE are JE virus proteins.

CV-1 cells infected with either v(JE, 100% E) or v(JE, 80% E) were labeled with $^{35}$S-methionine and the cell lysate prepared for immunoprecipitation using a hyperimmune ascitic fluid (HMAF). Analysis of immunoprecipitates showed that v(JE, 100% E) produced a protein of 53 kilodaltons (kd) similar in size to the E glycoprotein of JE virus (see FIG. 12). Digestion with endoglycosidase (endo) H, or endo F reduced the molecular size of the E product by 2–3 kd, a value consistent with the predicted structure that the full-length E protein product contained a mannose-rich carbohydrate side chain. The full-length E glycoprotein was not detected in the medium fraction of recombinant virus infected cells.

In the lysate fraction of recombinant v(JE, 80% E) infected cells, HMAF precipitated a 42 kd protein which was the size predicted for 80% E. Like the full-length E, 80% E contained a carbohydrate moiety of the mannose-rich type as it was sensitive to endo F or endo H digestion. Recombinant v(80% E) infected cells also secreted the E product extracellularly. The extracellular 80% E was completely resistant to endo H digestion indicating that 80% E had entered the secretary pathway through the Golgi apparatus and the carbohydrate moiety had been modified during the export process. The results showed that truncation at the C-terminus of JEV E to the size of 80% E altered its intracellular processing pathway resulting in extracellular secretion.

(12). Detection of JEV E on the cell surface.

Cells infected with v(JE, 100% E) or v(JE, 80% E) and labeled with $^{35}$S-methionine for 2 hr were analyzed for JEV E on the cell surface by binding to HMAF prior to their lysis. In a parallel experiment, cells similarly infected and labeled were lysed and the lysate used for immunoprecipitation by HMAF. The level of the full-length E or 80% E secreted into the medium of the recombinant infected cells was also analyzed by immunoprecipitation.

The results in FIG. 13 show the analysis of the full-length and truncated JEV E's in the immunoprecipitates by polyacrylamide gel electrophoresis. Full-length JEV E was predominantly found in the cell lysate fraction, only a low level (1–5%) was detected on the cell surface. Other labeled bands present in the immunoprecipitates were presumably background since they were also seem in the vSC8 control. On the other hand, JEV 80% E was readily detected on the cell surface in an amount varying from 10–25% of 80% E in the cell lysate dependent on experiments. In this study, the amount of 80% E secreted into the medium was estimated to be 6–10% of the total labeled 80% E product.

(13). Protective efficacy of full-length and C-terminally truncated 80% E's in mice.

Recombinant vaccinia virus v(JE, 100% E)j expressing the full-length E, or v(JE 80% E) expressing the 80% E of JEV was used for immunization of outbred CD-1 mice. The protective efficacies induced by these recombinants were evaluated following intraperitoneal challenge with a JE virus. Two separate protection experiments were performed. As shown below in Table III, both experiments showed that 80% E induced a complete or nearly complete protection (80–100% survival rate) whereas the full-length E induce only partial protection at a survival rate of 50–60%. A comparison of cummulative survival rates showed that immunization with 80% E induced a significantly higher level of resistance to JEV challenge than that afforded by immunization with the full-length E (P<0.006). These results are consistent with the view that 80% E of JEV exhibits increased protective immunity in mice.

TABLE III

IMMUNIZATION OF OUTBRED CD-1 MICE WITH RECOMBINANT VACCINIA VIRUS EXPRESSING C-TERMINALLY TRUNCATED 80% JE E INDUCES A HIGH LEVEL OF PROTECTION AGAINST LETHAL JE VIRUS CHALLENGE

| Recombinant Vaccinia | No. of Mice Survived/No. of Mice Tested Following 100 LD$_{50}$ Challenge | | Cumulative Survival |
|---|---|---|---|
| Virus | Exp. 1 | Exp. 2 | Rate |
| v (JE, 100% E) | 7/14 | 8/13 | 15/27 |
| v (JE, 80% E) | 11/14 | 15/15 | 26/29 |
| vSC8 (Control) | 1/15 | 2/13 | 3/28 |

Three week old CD-1 mice were inoculated intraperitoneally with $3 \times 10^6$ pfu/dose of recombinant vaccinia virus twice at two week interval (day 0 and day 14) followed by challenge with virulent JE virus (strain SA-14) on day 21. Animals were observed for symptoms of encephalitis and death following challenge.

(14). Analysis of sero-response by radio-immunoprecipitation.

Figures 14A, 14B:
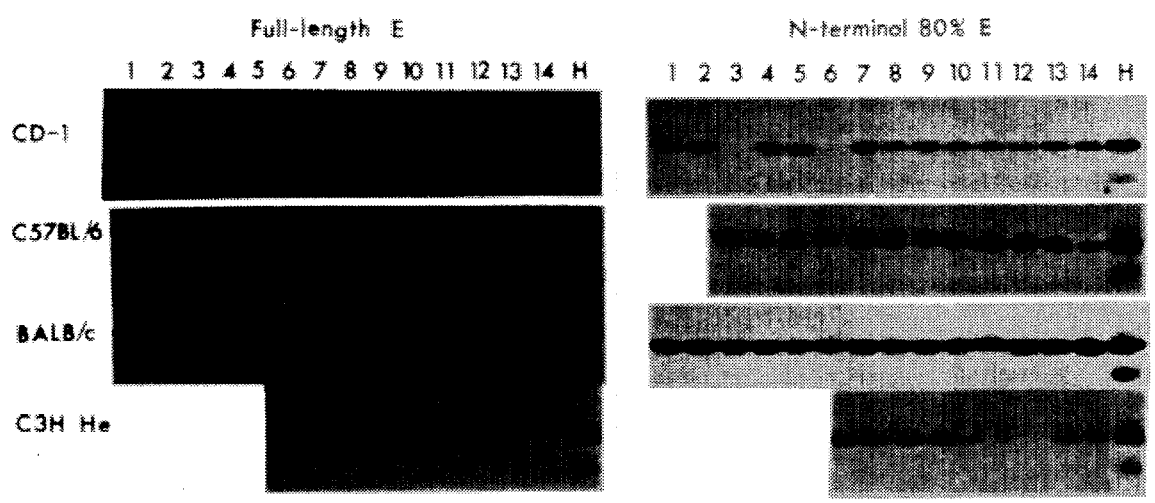
FIG. 14 Analysis of sero-response by radio-immunoprecipitation. Serum samples from CD-1 mice used for the challenge study and from the three inbred strains of mice used for the immunogenicity study were analyzed by radio-immunoprecipitation. The radio-labeled immunoprecipitates were separated on polyacrylamide gels. Sera of mice immunized with v (JE, 100% E) which expresses the full-length E are shown on the left; sera of mice immunized with v (JE, 80% E) which expresses the C-terminally truncated E are shown on the right. A lysate from $^{35}$S-methionine-labeled, JE virus-infected cells was used as the labeled antigen. Lane H is the control showing the E specific band as immunoprecipitated by JE HMAF.

Sera from outbred CD-1 mice immunized with recombinant v(JE, 100% E) or v(JE, 80% E) were analyzed by radio-immunoprecipitation in order to determine whether antibodies play a role in the protection of mice against JE virus infection. The levels of E antibodies were examined by the intensities of labeled E in the precipitates after separation on polyacrylamide gels (FIG. 14). The levels of E antibodies developed following immunization with v(JE, 100% E) varied among individual mice and E specific antibodies were low or not detected in 8 of the 14 serum samples.

On the other hand, sera from mice immunized with v(JE, 80% E) contained E antibodies that were detected at a uniformly high level with the exception of two sera in which E antibodies were low or not detected. The high level of E antibodies developed following immunization with v(JE, 80% E) appeared to correlate with the increased protection rate. Such variation of antibody response among individual CD-1 mice was consistently observed in both protection experiments. Since all CD-1 mice were inoculated twice with $3 \times 10^6$ pfu/dose of a recombinant virus, the variability of antibody response might stem from the background genetic heterogeneity of outbred mice.

To test for this possibility and to further evaluate the immunogenicity of 100% E and 80% E, inbred mice strain C57BL/6 of the H2-b haplotype strain BALB/c of the H2-d haplotype, and strain C3H/He of the H2-k haplotype were used for immunization with v(JE, 100% E), or v(JE, 80% E). Sera from immunized inbred mice were similarly analyzed by radio-immunoprecipitation as described. It can be seen in FIG. 14 that E antibodies were detected at a uniformly high level in C57BL and BALB/c mice immunized with v(JE, 80% E). In contrast, most mice immunized with v(JE, 100% E) developed a low level of E antibodies. Interestingly, C3H/He mice immunized with v(JE, 100% E) developed very low or not whereas antibodies were detected at a significant higher level in mice immunized with v(JE, 80% E). These studies showed that 80% E induced a more uniform and a higher level of antibody response than did the full-length E in several strains of inbred mice tested. Antibody response to 80% E JE was highest in BALB/c mice of the H-2d Haplotype and lowest in C3H/He mice belonging to the H-2-K Haplotype.

(15). Analysis of sero-response by ELISA and by plaque-reduction neutralization test.

The inventors also performed ELISA and a plaque-reduction neutralization test to analyze the level of E antibodies in sera of mice in order to further characterize the antibody response to immunization. Pooled sera from CD-1 mice that were immunized with v(JE, 100% E), or v(JE, 80% E) and pooled sera from each strain of inbred mice similarly immunized were tested. As can be seen in Table IV, antibodies in sera of CD-1 mice immunized with v(JE, 80% E) showed an 8-fold increase of the ELISA titer compared to antibodies in pooled sera of mice immunized with v(JE, 100% E). An increase of the antibody titer in sera of CD-1 mice immunized with v(JE, 80% E) was also observed when tested by virus neutralization. This indicates that neutralizing antibodies induced by the C-terminally truncated E play a role in mediating resistance against JE virus infection. Similarly, the results from studies using the three strains of inbred mice also showed that v(JE, 80% E) exhibit increased immunogenicity compared to v(JE, 100% E) as evaluated by ELISA and by virus neutralization.

TABLE IV

ANALYSIS OF SERA FROM MICE IMMUNIZED WITH RECOMBINANT VACCINIA VIRUS EXPRESSING FULL-LENGTH OR 80% E

| Mouse Strain | Recombinant Virus | ELISA Titer ($\times 10^3$)* Reciprocal | Neutralization (50% Plaque Reduction) Reciprocal |
|---|---|---|---|
| CD-1 | v (JE, 100% E) | 8 | <10 |
|  | v (JE, 80% E) | 64 | 50 |
| C3H | v (JE, 100% E) | 4 | <10 |
|  | v (JE, 80% E) | 16 | <10 |
| C57BL | v (JE, 100% E) | 4 | <10 |
|  | v (JE, 80% E) | 16 | 60 |
| BALB/c | v (JE, 100% E) | 8 | <10 |
|  | v (JE, 80% E) | 128 | 30 |

*The negative control from VSC8 gave a value of <1000, serum titer was the highest dilution that gave OD of 0.2 or more.

All publications mentioned hereinabove are hereby incorporated by reference.

While the foregoing invention has been described in some detail for purposes of clarity and understanding, it will be clear to one skilled in the art from a reading of this disclosure that various changes in form and detail can be made without departing from the true scope of the invention.

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GATCCTAGCT AGCTAGGTAC C                                                            2 1

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GATCGGTACC TAGCTAGCTA G                                                           2 1

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

TGAATGAATG AGATCTGGTA C                                                           2 1

( 2 ) INFORMATION FOR SEQ ID NO:4:

( i ) SEQUENCE CHARACTERISTICS:
        ( A ) LENGTH: 17 base pairs
        ( B ) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:4:

CAGATCTCAT TCATTCA                        17

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CGTTTGCCAT ACGCTCACAG                     20

(2) INFORMATION FOR SEQ ID NO:6:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

AGATCTGGTA CCTAGGAACT CCCTTTCCTG AA        32

(2) INFORMATION FOR SEQ ID NO:7:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

AGATCTGGTA CCTAACTCCC TTTCCTGAAC CA        32

(2) INFORMATION FOR SEQ ID NO:8:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

AGATCTGGTA CCTACCCTTT CCTGAACCAA TG        32

(2) INFORMATION FOR SEQ ID NO:9:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

( x i ) SEQUENCE DESCRIPTION: SEQ ID NO:9:

AGATCTGGTA CCTATTTCCT GAACCAATGG AG 32

( 2 ) INFORMATION FOR SEQ ID NO:10:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

AGATCTGGTA CCTACCTGAA CCAATGGAGT GT 32

( 2 ) INFORMATION FOR SEQ ID NO:11:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

GATCTATGAC TGTCTTCTTT GTCCTAA 27

( 2 ) INFORMATION FOR SEQ ID NO:12:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

AACAACGGAT CCATGGTGGT GTTTACCATC CTCCTG 36

( 2 ) INFORMATION FOR SEQ ID NO:13:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

CACATGGATC CTAAGCATGC ACATTGGTCG CTAA 34

( 2 ) INFORMATION FOR SEQ ID NO:14:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

GCCTAGGGAT CCTCAAGCTT TGTGCCAATG GTGGTT 36

( 2 ) INFORMATION FOR SEQ ID NO:15:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:15:

```
Arg Lys Gly Ser Ser Ile Gly Lys
1               5
```

What is claimed is:

1. A vaccine composition for humans and animals against dengue virus or Japanese Encephalitis Virus (JEV) infection, comprising a recombinant virus expressing a C-terminally truncated flavivirus envelope protein, said truncated flavivirus envelope protein selected from the group consisting of:

amino acids 1–392, 1–393, 1–394, 1–395 or 1–396 of dengue type 4 envelope glycoprotein (amino acids 392–396 are set forth in FIG. 9);

a peptide from dengue type 1, type 2 or type 3 corresponding to amino acids 1–392, 1–393, 1–394, 1–395 or 1–396 of dengue type 4 envelope glycoprotein (amino acids 392–396are set forth in FIG. 9); and amino acids 1–398, 1–399, 1–400, 1–401 or 1–402 of Japanese encephalitis virus (amino acids 398–402 are set forth in FIG. 11), wherein said virus is present in said composition in an amount sufficient to induce immunity against said infection; and wherein said composition further comprises a pharmaceutically acceptable carrier.

2. The vaccine composition according to claim 1 wherein said recombinant virus is a vaccinia virus.

3. A vaccine composition for humans and animals against dengue virus or Japanese Encephalitis Virus (JEV) infection comprising a recombinantly expressed truncated flavivirus envelope protein, said truncated flavivirus envelope protein selected from the group consisting of:

amino adds 1–392, 1–393, 1–394, 1–395 or 1–396 of dengue type 4 envelope glycoprotein (amino acids 392–396 are set forth in FIG. 9);

a peptide from dengue type 1, type 2 or type 3 corresponding to amino acids 1–392, 1–393, 1–394, 1–395 or 1–396 of dengue type 4 envelope glycoprotein (amino acids 392–396 are set forth in FIG. 9); and amino acids 1–398, 1–399, 1–400, 1–401 or 1–402 of Japanese encephalitis virus (amino acids 398–402 are set forth in FIG. 11), wherein said envelope protein is present in said composition in an amount sufficient to induce immunity against said infection; and wherein said composition further comprises a pharmaceutically acceptable carrier.

4. The vaccine composition according to claim 3 which further comprises an adjuvant.

5. A DNA construct consisting essentially of a vector and a DNA segment encoding a C-terminally truncated dengue virus or Japanese encephalitis virus (JEV) envelope protein, said truncated flavivirus envelope protein selected from the group consisting of:

amino acids 1–392, 1–393, 1–394, 1–395 or 1–396 of dengue type 4 envelope glycoprotein (amino acids 392–396 are set forth in FIG. 9);

a peptide from dengue type 1, type 2 or type 3 corresponding to amino acids 1–392, 1–393, 1–394, 1–395 or 1–396 of dengue type 4 envelope glycoprotein (amino acids 392–396 are set forth in FIG. 9); and amino acids 1–398, 1–399, 1–400, 1–401 or 1–402 of Japanese encephalitis virus (amino acids 398–402 are set forth in FIG. 11).

6. The DNA construct according to claim 5 wherein said vector is selected from the group consisting of a vaccinia virus vector and a baculovirus vector.

7. A recombinant virus encoding a C-terminally truncated dengue virus or Japanese encephalitis virus (JEV) envelope protein, said truncated flavivirus envelope protein selected from the group consisting of:

amino acids 1–392, 1–393, 1–394, 1–395 or 1–396 of dengue type 4 envelope glycoprotein (amino acids 392–396 are set forth in FIG. 9);

a peptide from dengue type 1, type 2 or type 3 corresponding to amino acids 1–392, 1–393, 1–394, 1–395 or 1–396 of dengue type 4 envelope glycoprotein (amino acids 392–396 are set forth in FIG. 9); and amino acids 1–398, 1–399, 1–400, 1–401 or 1–402 of Japanese encephalitis virus (amino acids 398–402 are set forth in FIG. 11).

8. The recombinant virus according to claim 7 which is selected from the group consisting of a vaccinia virus and a baculovirus.

9. A host cell productively infected with the recombinant virus according to claim 7 which expresses said truncated protein encoded in said virus.

10. The host cell according to claim 9 wherein said host cell is selected from the group consisting of a mammalian cell and an insect cell.

11. The host cell according to claim 10 wherein said host cell is selected from the group consisting of a CV-1 and a *Spodoptera frugiperda* (Sf9) cell.

12. A recombinant, C-terminally truncated dengue virus or Japanese encephalitis virus (JEV) envelope protein selected from the group consisting of:

amino acids 1–392, 1–393, 1–394, 1–395 or 1–396 of dengue type 4 envelope glycoprotein (amino acids 392–396 are set forth in FIG. 9);

a peptide from dengue type 1, type 2 or type 3 corresponding to amino acids 1–392, 1–393, 1–394, 1–395 or 1–396 of dengue type 4 envelope glycoprotein (amino acids 392–396 are set forth in FIG. 9); and amino acids 1–398, 1–399, 1–400, 1–401 or 1–402 of Japanese encephalitis virus (amino acids 398–402 are set forth in FIG. 11).

13. The protein according to claim 12 wherein said protein is glycosylated.

14. The protein according to claim 12, wherein said protein is expressed by a virus in a host cell intracellularly, extracellularly or on the outer membrane of said host cell.

* * * * *

UNITED STATES PATENT AND TRADEMARK OFFICE
CERTIFICATE OF CORRECTION

PATENT NO. : 5,494,671
DATED : February 27, 1996
INVENTOR(S) : Ching-Jun Lai et al.

It is certified that error appears in the above-identified patent and that said Letters Patent is hereby corrected as shown below:

Column 33,
Line 22, delete "adds" and insert -- acids --.

Signed and Sealed this

Eleventh Day of November, 2003

JAMES E. ROGAN
*Director of the United States Patent and Trademark Office*